US008889423B2

(12) United States Patent
Oda et al.

(10) Patent No.: US 8,889,423 B2
(45) Date of Patent: *Nov. 18, 2014

(54) METHOD FOR ANALYSIS OF COMPOUND-BINDING ABILITY OF PROTEIN

(75) Inventors: Yoshiya Oda, Tsukuba (JP); Hiroyuki Katayama, Tsukuba (JP)

(73) Assignee: Eisai R & D Management Co., Ltd., Tokyo (JP)

(*) Notice: Subject to any disclaimer, the term of this patent is extended or adjusted under 35 U.S.C. 154(b) by 706 days.

This patent is subject to a terminal disclaimer.

(21) Appl. No.: 11/989,565

(22) PCT Filed: Jul. 31, 2006

(86) PCT No.: PCT/JP2006/315545
§ 371 (c)(1),
(2), (4) Date: Jan. 28, 2008

(87) PCT Pub. No.: WO2007/013699
PCT Pub. Date: Feb. 1, 2007

(65) Prior Publication Data
US 2009/0148960 A1  Jun. 11, 2009

(30) Foreign Application Priority Data
Jul. 29, 2005  (JP) .................. 2005-222097

(51) Int. Cl.
G01N 30/02  (2006.01)
G01N 24/00  (2006.01)
C07K 1/22  (2006.01)
G01N 30/84  (2006.01)
H01J 49/04  (2006.01)
G01N 33/68  (2006.01)
G01N 30/72  (2006.01)

(52) U.S. Cl.
CPC ............ G01N 33/6848 (2013.01); G01N 30/84 (2013.01); G01N 2030/027 (2013.01); H01J 49/0409 (2013.01); G01N 2030/8411 (2013.01); G01N 30/72 (2013.01)
USPC ............ 436/161; 436/173; 422/70; 73/61.52; 73/61.56; 530/413

(58) Field of Classification Search
None
See application file for complete search history.

(56) References Cited

U.S. PATENT DOCUMENTS

| | | | | |
|---|---|---|---|---|
| 5,674,987 | A | 10/1997 | Gray | |
| 5,763,586 | A | 6/1998 | Gray | |
| 7,846,748 | B2* | 12/2010 | Borchers | 436/523 |
| 7,868,547 | B2* | 1/2011 | Pappin et al. | 313/564 |
| 2003/0091976 | A1* | 5/2003 | Boschetti et al. | 435/4 |
| 2003/0119062 | A1* | 6/2003 | Brame | 435/7.1 |
| 2008/0057592 | A1* | 3/2008 | Oda | 436/86 |

FOREIGN PATENT DOCUMENTS

| | | | |
|---|---|---|---|
| JP | 2004-516486 | 6/2004 | |
| JP | 2005-503557 | 2/2005 | |
| WO | WO 97/43301 | * 11/1997 | ............... C07K 1/04 |
| WO | WO 02/052271 A2 | 7/2002 | |
| WO | WO 03/025576 A2 | 3/2003 | |
| WO | WO-03/054549 A2 | 7/2003 | |

OTHER PUBLICATIONS

Tian et al., "Characterization of small-molecule-biomacromolecule interactions: From simple to complex",Trends in Analytical Chemistry, vol. 24, No. 9, pp. 810-825 (2005).
Supplementary European Search Report dated Dec. 2, 2010 in connection with European Patent Application No. 06796301.
Borch, J. et al.; "Screening for Enzyme Inhibitors by Surface Plasmon Resonance Combined with Mass Spectrometry"; Analytical Chemistry, vol. 76, No. 18, Sep. 15, 2004, pp. 5243-5248.
Zhang, B., et al.; "Frontal Affinity Chromatography Coupled to Mass Spectrometry for Screening Mixtures of Enzyme Inhibitors"; Analytical Biochemistry, 299, 2001, pp. 173-182.
Sechi, S.; "A method to identify and simultaneously determine the relative quantities of proteins isolated by gel electrophoresis"; Rapid Communications in Mass Spectrometry, 16, 2002, pp. 1416-1424.
Gygi, Steven P. et al.; :Quantitive analysis of complex protein mistrues using isotope-coded affinity tags; Nature Biotechnology, vol. 17, Oct. 1999, pp. 994-999.
Neubauer, G. et al.; "Mass spectrometry and EST-database searching allows characterization of the multi-protein spliceosome complex"; Nature Genetics, vol. 20, Sep. 1998, pp. 46-50.
Wigge, Philip A., et al.; "Analysis of the *Saccharomyces* Spindle Pole by Matrix-assisted Laser Desorption/Ionization (MALDI) Mass Spectrometry"; The Journal of Cell Biology, vol. 141, 1998, pp. 967-977.
Rout, Michael, P., et al.; "The Yeast Nuclear Pore Complex: Composition, Architecture, and Transport Mechanism"; vol. 148, Feb. 21, 2000, pp. 635-651.

(Continued)

Primary Examiner — Christine Foster
(74) Attorney, Agent, or Firm — Dickstein Shapiro LLP

(57) ABSTRACT

A method for analyzing a binding ability of protein to a compound, comprising the steps of (a) fractionating a first group of isotope-labeled proteins into plural fractions using a carrier having the compound immobilized thereon; (b) fractionating a second group of proteins into one or plural fractions using a carrier having the compound immobilized thereon; (c) adding an amount of at least one fraction obtained in step (b) to each of the fractions obtained in step (a); (d) analyzing the fractions obtained in step (c) with mass spectrometry; and (e) based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

6 Claims, 6 Drawing Sheets

(56) References Cited

OTHER PUBLICATIONS

Gavin, Anne-Claude, et al.; "Functional organization of the yeast proteome by systematic analysis of protein complexes"; Nature, vol. 415, Jan. 2002, pp. 141-147.
Ho, Yuen, et al.; "Systematic identification of protein complexes in *Saccharomyces cerevisiae* by mass spectrometry"; Nature, vol. 415, Jan. 2002, pp. 180-183.
Drewes, Gerard, et al.; "Global approaches to protein-protein interactions"; Current Opinion in Cell Biology, 2003, 15, pp. 199-205.
Gavin, Anne-Claude, et al.; "Protein complexes and proteome organization from yeast to man"; Current Opinion in Chemical Biology 2003, 7, pp. 21-27.
Katayama, Hiroyuki, et al.; "Efficient in-gel digestion procedure using 5-cyclohexyl-1-pentyl-β-D-maltoside as an additive for gel-based membrane proteomics"; Rapid Communications in Mass Spectrometry, 2004, 18, pp. 2388-2394.
Ishihama, Yasushi, et al.; "Microcolumns with self-assembled particle frits for proteomics"; Journal of Chromatography A, 979, 2002, pp. 233-239.
International Search Report issued for PCT/JP2006/315545, date of mailing Sep. 5, 2006 (with English translation).
Written Opinion issued for PCT/JP2006/315545, dated Sep. 5, 2006.
International Preliminary Report on Patentability issued for PCT/JP2006/315545, date of issuance Jan. 29, 2008 (with English translation).
Response to Search Opinion filed on Jun. 28, 2011 with the European Patent Office, in connecton with EP Appl. No. 06796301.

* cited by examiner

METHOD FOR ANALYSIS OF COMPOUND-BINDING ABILITY OF PROTEIN

CROSS-REFERENCE TO RELATED APPLICATIONS

This application is a U.S. National Phase Application of PCT International Application No. PCT/JP2006/315545, filed on Jul. 31, 2006, which claims priority to Japanese Patent Application No. 2005-222097, filed Jul. 29, 2005, which is hereby incorporated herein by reference.

TECHNICAL FIELD

The present invention relates to a method for analyzing a binding ability of protein to a compound using mass spectrometry.

BACKGROUND OF THE INVENTION

Analysis of protein-protein binding gives us a lot of useful information for studying functions of each protein. Analysis of binding between a compound available for a drug and protein gives us important information for revealing influences of such a compound on living organisms.

For analyzing the binding between a substance and protein, not only the specificity of the protein which binds to the substance, and but also the binding ability between the substance and protein (also referred to as the "binding activity"), are also important indicators.

For example, when an inhibitor against an enzyme is developed, if the binding ability of the inhibitor to the enzyme is lower than the binding ability of the original substrate of the enzyme to the enzyme, the inhibitor cannot fully function as an inhibitor.

The binding ability between molecules is generally represented by the binding constant (or dissociation constant). When two substances to be bound together are in an antigen-antibody relationship, the binding constant can be calculated by ELISA or RIA. Even when two substances to be bound together are in a relationship other than the antigen-antibody relationship, the binding constant can be obtained by equilibrium dialysis, fluorescence quenching, atomic force microscope, quartz vibrator, surface plasmon resonance, frontal affinity chromatography or other methods (see document (1) document (2)). However, in order to use these methods, it is required that both of the substances should be already known and that both of the substances should be purified and isolated before measurement. Therefore, these methods cannot be used for studying the binding ability of a substance to each of proteins contained in a mixture of plural kinds of unknown proteins.

(1) Borch, J., Roepstorff, P., Anal. Chem. 2004, 76, 5243-5248.
(2) Zhang, B., Palcic, M. M., Schriemer, D. C., Alvarez-Manilla, G, Pierce, M., Hindsgaul, O., Anal. Biochem. 2001, 299, 173-182.

DISCLOSURE OF THE INVENTION

The present invention has an object of providing a method and a system for analyzing a binding ability of protein to a compound using a labeling method or a protein quantitation method and mass spectrometry.

As a result of active studies performed to solve the above-described problems, the present inventor found that a binding ability of protein to a compound can be analyzed (compared) as follows. Protein bound to a compound immobilized on a carrier is fractionated into plural fractions. Performing fractionation separately, one fraction, or a mixture of all the fractions or a mixture of plural contiguous fractions, is prepared as an internal standard fraction. A certain amount of the internal reference fraction is added to each of the above-obtained fractions, and each of the fractions is analyzed with mass spectrometry. Then, a peak intensity ratio is detected based on the mass spectrometry information. By this, the binding ability of protein to the compound can be analyzed (compared). Thus, the present inventor completed the present invention.

The present invention is directed to the following.

(1) A method for analyzing a binding ability of protein to a compound, comprising the steps of:
  (a) fractionating a first group of isotope-labeled proteins into plural fractions using a carrier having the compound immobilized thereon;
  (b) fractionating a second group of proteins into one or plural fractions using a carrier having the compound immobilized thereon;
  (c) adding a certain amount of the one fraction obtained in step (b), or a certain amount of a mixture of all the fractions or a mixture of plural contiguous fractions among the fractions obtained in step (b), to each of the fractions obtained in step (a);
  (d) analyzing the fractions obtained in step (c) with mass spectrometry; and
  (e) based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

(2) A method for analyzing a binding ability of protein to a compound, comprising the steps of:
  (a) fractionating a first group of proteins into plural fractions using a carrier having the compound immobilized thereon;
  (b) fractionating a second group of isotope-labeled proteins into one or plural fractions using a carrier having the compound immobilized thereon;
  (c) adding a certain amount of the one fraction obtained in step (b), or a certain amount of a mixture of all the fractions or a mixture of plural contiguous fractions among the fractions obtained in step (b), to each of the fractions obtained in step (a);
  (d) analyzing the fractions obtained in step (c) with mass spectrometry; and
  (e) based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

(3) A method for analyzing a binding ability of protein to a compound, comprising the steps of:
  (a) fractionating a first group of proteins into plural fractions using a carrier having the compound immobilized thereon;
  (b) fractionating a second group of proteins into one or plural fractions using a carrier having the compound immobilized thereon;
  (c) labeling the fractions obtained in step (a);

(d) adding a certain amount of the one fraction obtained in step (b), or a certain amount of a mixture of all the fractions or a mixture of plural contiguous fractions among the fractions obtained in step (b), to each of the fractions labeled in step (c);

(e) analyzing the fractions obtained in step (d) with mass spectrometry; and (f) based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

(4) A method for analyzing a binding ability of protein to a compound, comprising the steps of:

(a) fractionating a first group of proteins into plural fractions using a carrier having the compound immobilized thereon;

(b) fractionating a second group of proteins into one or plural fractions using a carrier having the compound immobilized thereon;

(c) labeling the one fraction obtained in step (b), or a mixture of all the fractions or a mixture of plural contiguous fractions among the fractions obtained in step (b);

(d) adding a certain amount of the fraction or the mixture labeled in step (c) to each of the fractions obtained in step (a);

(e) analyzing the fractions obtained in step (d) with mass spectrometry; and (f) based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

(5) The method according to any one of (1) through (4), wherein step (a) of fractioning and/or step (b) of fractioning is the step of performing the fractioning by changing the strength of an eluting solvent.

(6) The method according to any one of (1) through (5), further comprising the step of identifying each protein contained in each fraction based on the mass spectrometry information.

In (1) through (6) above, the second group of proteins may be added in a certain amount to each of the fractions derived from the first group of proteins without being fractionated into one or plural fractions using the carrier having the compound immobilized thereon.

In (1) through (6) above, the binding ability of protein to the compound may be analyzed by using a protein quantitation method or by using an EMPAI of the protein as an index, instead of using a protein labeling method.

(7) A system for analyzing a binding ability of protein to a compound, comprising:

(a) means for fractionating a first group of isotope-labeled proteins into plural fractions using a carrier having the compound immobilized thereon;

(b) means for fractionating a second group of proteins into one or plural fractions using a carrier having the compound immobilized thereon;

(c) means for adding a certain amount of the one fraction obtained by means (b), or a certain amount of a mixture of all the fractions or a mixture of plural contiguous fractions among the fractions obtained by means (b), to each of the fractions obtained by means (a);

(d) means for analyzing the fractions obtained by means (c) with mass spectrometry; and (e) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(8) A system for analyzing a binding ability of protein to a compound, comprising:

(a) means for fractionating a first group of proteins into plural fractions using a carrier having the compound immobilized thereon;

(b) means for fractionating a second group of isotope-labeled proteins into one or plural fractions using a carrier having the compound immobilized thereon;

(c) means for adding a certain amount of the one fraction obtained by means (b), or a certain amount of a mixture of all the fractions or a mixture of plural contiguous fractions among the fractions obtained by means (b), to each of the fractions obtained by means (a);

(d) means for analyzing the fractions obtained by means (c) with mass spectrometry; and (e) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(9) A system for analyzing a binding ability of protein to a compound, comprising:

(a) means for fractionating a first group of proteins into plural fractions using a carrier having the compound immobilized thereon;

(b) means for fractionating a second group of proteins into one or plural fractions using a carrier having the compound immobilized thereon;

(c) means for labeling the fractions obtained by means (a);

(d) means for adding a certain amount of the one fraction obtained by means (b), or a certain amount of a mixture of all the fractions or a mixture of plural contiguous fractions among the fractions obtained by means (b), to each of the fractions labeled by means (c);

(e) means for analyzing the fractions obtained by means (d) with mass spectrometry; and (f) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(10) A system for analyzing a binding ability of protein to a compound, comprising:

(a) means for fractionating a first group of proteins into plural fractions using a carrier having the compound immobilized thereon;

(b) means for fractionating a second group of proteins into one or plural fractions using a carrier having the compound immobilized thereon;

(c) means for labeling the one fraction obtained by means (b), or a mixture of all the fractions or a mixture of plural contiguous fractions among the fractions obtained by means (b);

(d) means for adding a certain amount of the fraction or the mixture labeled by means (c) to each of the fractions obtained by means (a);

(e) means for analyzing the fractions obtained by means (d) with mass spectrometry; and (f) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(11) The system according to any one of (7) through (10), wherein means (a) for fractioning and/or means (b) for fractioning is means for performing the fractioning by changing the strength of an eluting solvent.

(12) The system according to any one of (7) through (11), further comprising means for identifying each protein contained in each fraction based on the mass spectrometry information.

In (7) through (12) above, the second group of proteins may be added in a certain amount to each of the fractions derived from the first group of proteins without being fractionated into one or plural fractions using the carrier having the compound immobilized thereon.

In (7) through (12) above, the binding ability of protein to the compound may be analyzed by using protein quantitation means or by using an EMPAI of the protein as an index, instead of using protein labeling means.

The present invention makes it possible to create rankings of the binding ability of plural kinds of substances (proteins) bindable to a compound. One embodiment of the present invention makes it possible to analyze a binding ability of plural kinds of unknown substances to a compound. One embodiment of the present invention is useful in being applicable even to the case where the target substance is unknown and the substances are not fully separated in a mixed sample.

DESCRIPTION OF THE REFERENCE NUMERALS

Figure 1:
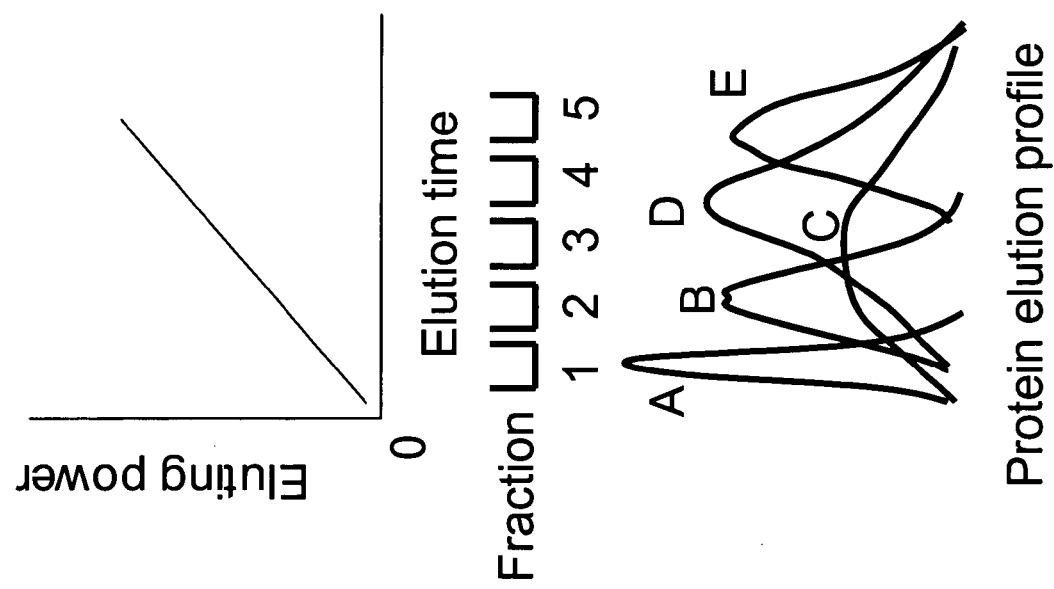
FIG. 1 shows an exemplary protein elution profile provided by affinity purification.

1a: tube; 1b: tube; 2a: stirring blade; 2b: stirring blade; 11a: culture device; 11b: culture device; 12a: culture liquid bottle; 12b: culture liquid bottle; 13a: cell crushing device; 13b: cell crushing device; 14: labeling device; 15a: carrier having a compound immobilized thereon; 15b: carrier having a compound immobilized thereon; 16a: protein fractionation control device; 16b: protein fractionation control device; 17a: purified protein separator; 17b: purified protein separator; 17c: mixing device; 18-1: tube; 18-2: tube; 18-3: tube; 18-4: tube; 18-5: tube; 19: plate; 20: mass spectrometry device; 21: computer; 30: central computer; 100: LAN; 301: control unit; 302: protein fractionation unit; 303: protein mixing unit; 304: mass spectrometry unit; 501: CPU; 502: transmission/receiving section; 503: input section; 504: output section; 505: ROM; 506: RAM; 507: hard disc drive (HDD); 508: CD-ROM drive; 509: protein database (DB); 510: CD-ROM; 511: Internet

BEST MODE FOR CARRYING OUT THE INVENTION

Hereinafter, embodiments of the present invention will be described. The following embodiments are given in order to illustrate the present invention and are not intended to limit the present invention in any way. The present invention can be carried out in various embodiments without departing from the gist thereof.

The documents, laid-open publications, patents and other patent documents cited in this specification are incorporated herein by reference. The claims and the disclosure of the specification, drawings and abstract of Japanese Application JP2005-222097 filed on Jul. 29, 2005, based upon which the present application claims the benefit of priority, are entirely incorporated herein by reference.

As used herein, the term "protein" encompasses a peptide comprising two or more amino acids bound together by peptide binding. The "protein" also encompasses physiologically modified proteins (e.g., phosphorylated protein, glycoprotein, etc.). As used herein, the term "group of proteins" refers to an assembly comprising two or more kinds of proteins.

As used herein, the term "labeled protein" refers to a protein in which a part of molecules forming the protein is labeled. Specifically, a protein labeled with an isotope is referred to as an "isotope-labeled protein". As used herein, the term "group of isotope-labeled proteins" refers to an assembly comprising two or more kinds of isotope-labeled proteins.

As used herein, the term "metabolically isotope-labeled protein" refers to a protein in which a part of molecules forming the protein is metabolically labeled with an isotope as a result of an isotope-labeled precursor of the protein (e.g., amino acid) being added. As used herein, the term "group of metabolically isotope-labeled proteins" refers to an assembly comprising two or more kinds of metabolically isotope-labeled proteins. The term "metabolically" refers to a physiological condition obtained via enzyme reaction or the like, and preferably refers to a metabolic reaction in a cultured cell.

1. Overview of the Present Invention

The present invention relates to a method for analyzing the degree of the binding ability of a group of known or unknown substances (proteins) bindable to a compound using mass spectrometry and creating rankings of the substances in accordance with the binding ability.

In general, for eluting a group of substances bound to a compound immobilized on carriers in a column which is filled with such carriers having the compound immobilized thereon (affinity chromatography column), the eluate is fractionated while the eluting power of the eluting solvent is gradually increased. Therefore, the last substance eluted from the affinity chromatography column has the highest binding ability to the compound immobilized on the carriers. For example, when proteins A-E are eluted from the affinity chromatography column as shown in FIG. 1, the proteins contained in fraction 5 have the highest binding ability. It is assumed that the proteins contained in fraction 5 are identified to be three kinds of proteins C, D and E. In order to compare the degrees of the binding ability of the proteins C, D and E, the elution profile of each protein is checked using a standard product of thereof, or using a different fluorescent color tag or a different epitope tag. As a result, it is found that the protein E is eluted at the latest, namely, has the highest binding ability.

However, the protein eluted from the affinity chromatography column may be entirely eluted in one fraction or may be eluted over a wide range from the first fraction to the last fraction. Moreover, one fraction contains plural kinds of proteins in a mixed state. For these reasons, it is not easy to find the elution pattern of each protein. Preparation of a standard product or introduction of a tag is not easy and cannot be done routinely. Introduction of a tag also causes an artificial influence and prevents a true binding ability from being found. In addition, when these methods are used, it is necessary to identify the bound proteins in advance.

In the present invention, a group of proteins are fractionated into plural fractions using a carrier having a compound immobilized thereon. Separately, another group of proteins are fractionated into one or plural fractions using a carrier having the compound immobilized thereon, and a mixture of all the obtained fractions or a mixture of plural contiguous fractions is prepared as an internal standard fraction. Among the groups of proteins to be loaded to a column filled with carries having the compound immobilized thereon (affinity chromatography column), one group of proteins are isotope-labeled (or are isotope-labeled after being fractionated). Next, a certain amount of the mixture of all the fractions (or of plural contiguous fractions) as the internal standard fraction is added to each test sample separately fractionated therefrom. Optionally, the fractions may be separated by SDS-PAGE or the like so that the proteins are digested with trypsin or the like. Then, each fraction is measured by a mass spectrometry device.

Figure 2:
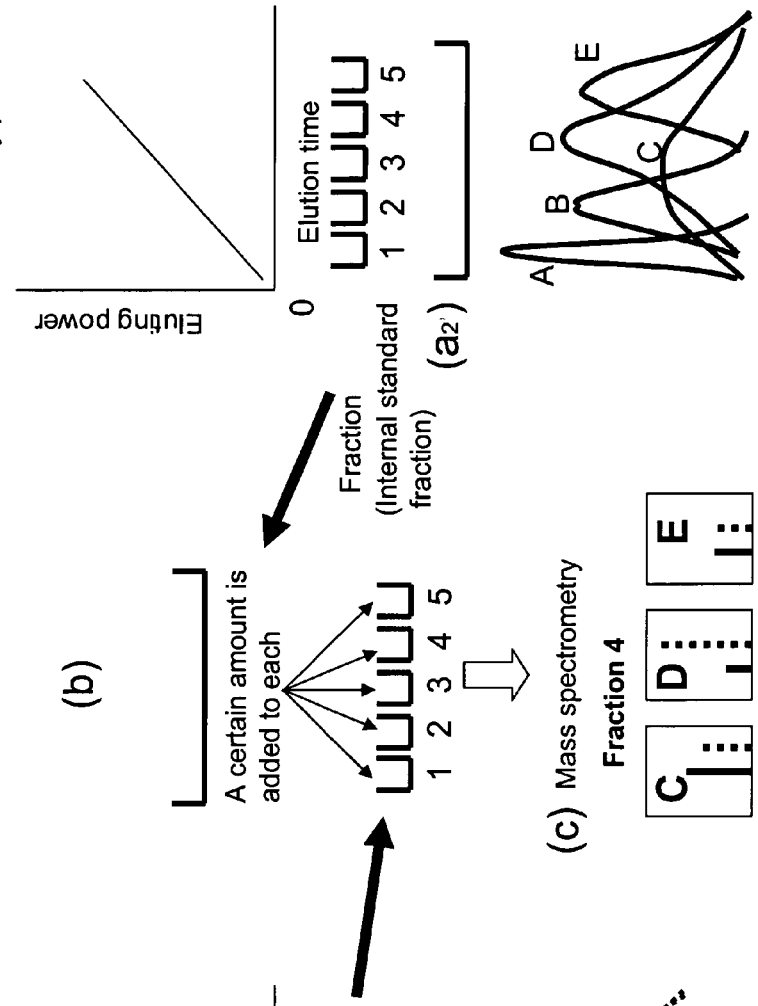
FIG. 2 shows an overview of a method of the present invention.

Either the fractionated test samples or the internal standard fraction sample is isotope-labeled. FIG. 2 shows an embodiment in which the test samples are isotope-labeled before affinity purification (FIG. 2, $a_1$). The fractions obtained by affinity purification of labeled samples (FIG. 2, $a_1$) and the fractions obtained by affinity purification of unlabeled samples (FIG. 2, $a_2$) are mixed together (FIG. 2, $b$), and the mixed samples are analyzed with mass spectrometry (FIG. 2, $c$). The mass spectrum shows the peaks of the proteins derived from the isotope-labeled fractions (FIG. 2, $c$, peaks represented with dashed lines) and the peaks of the proteins derived from the unlabeled fractions (FIG. 2, $c$, peaks represented with solid lines) in pairs. The intensity ratios of the peaks are obtained. In the case where a protein is eluted in plural fractions, that protein is eluted while being most concentrated in the fraction having the highest peak intensity ratio. In the case where plural kinds of proteins are contained in one fraction, the protein having the highest peak intensity ratio is eluted while being most concentrated in that fraction. For example, referring to FIG. 2, of proteins A-E, proteins C and D are contained in a larger amount in fraction 4 than in fraction 5, whereas the protein E is contained in a larger amount in fraction 5 than in fraction 4 (FIG. 2, $c$). In fraction 4, protein D has the highest peak intensity ratio; whereas in fraction 5, protein E has the highest peak intensity ratio. By comparing protein D and protein E based on these, it is found that the proteins are fractionated in the order of protein D and then protein E, and that protein E is eluted at the latest.

In the step shown in FIG. 2, $b$, it is not necessary to mix all the fractions as the internal standard fraction, but only the continuous fractions to be compared may be mixed. For example, when fractions 3, 4 and 5, or proteins C, D and E are the test target, the continuous fractions, i.e., only fractions 3, 4 and 5 may be mixed to obtain the internal standard fraction. This can prevent the situation where the internal standard fraction is entirely diluted and the target substance cannot be detected. All the amount of each fraction may be mixed to obtain the internal standard fraction, or a certain amount of each fraction may be mixed to obtain the internal standard fraction. Regarding the step of fractionating the unlabeled samples into one or plural fractions (FIG. 2, $a_2$), in the case where the samples are fractionated into one fraction, that one fraction may be used as the internal standard fraction (FIG. 2, $a_{2'}$).

It is found in which fraction each protein is most concentrated when being eluted, and a protein concentrated in a fraction which is eluted later can be determined to have a higher binding ability to the compound immobilized on the carrier. It is not absolutely necessary to fractionate the samples for the internal standard fraction using a carrier having the compound immobilized thereon. However, many of the proteins detected by a mass spectrometry device from a sample which is not concentrated are expressed in a very large amount. In addition, a protein which is not concentrated and a protein concentrated with a carrier having the compound immobilized thereon have different concentrations. In this case, considering the narrowness of the dynamic range of the mass spectrometry, it is difficult to adjust the amount of the internal standard fraction. For these reasons, it is desirable to concentrate the samples for the internal standard fraction also with a carrier having the compound immobilized thereon.

The present invention makes it possible to calculate the binding ability degree ratio of plural kinds of proteins to a compound. Therefore, the analysis of the present invention may be conducted on plural kinds of compounds so as to calculate the correlation of the binding ability between compounds and proteins. Thus, the characteristics of these compounds to living organisms, cells or the like can be analyzed.

2. Embodiments of the Present Invention (1) First Embodiment

A first embodiment of the present invention comprises the following steps for analyzing a binding ability of protein to a compound, wherein the group of proteins as the target of analysis are isotope-labeled before fractionation:

(a) step of fractionating a first group of isotope-labeled proteins into plural fractions using a carrier having the compound immobilized thereon;
(b) step of fractionating a second group of proteins into one or plural fractions using a carrier having the compound immobilized thereon;
(c) step of adding a certain amount of the one fraction obtained in step (b), or a certain amount of a mixture of all the fractions or a mixture of plural contiguous fractions among the fractions obtained in step (b), to each of the fractions obtained in step (a);
(d) step of analyzing the fractions obtained in step (c) with mass spectrometry; and
(e) step of, based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

(a) The Step of Fractionating a First Group of Isotope-Labeled Proteins into Plural Fractions Using a Carrier Having the Compound Immobilized Thereon In the present invention, the first group of proteins are protein samples as the target of analysis, for which samples obtained from, for example, tissues, bodily fluids from living organisms, cells, cell organella, protein composites and the like are usable.

For the group of isotope-labeled proteins, any protein in which a part of molecules (amino acids) forming the protein is labeled with an isotope may be used. There is no specific limitation on the method for preparation or the labeling site.

Hereinafter, a specific method for preparation will be described.

The group of isotope-labeled proteins may be prepared by metabolic isotope labeling. For example, a protein in a cell may be metabolically isotope-labeled by culturing a culturable cell in a medium containing an isotope-labeled precursor of the protein (e.g., amino acid). Any culturing condition is usable. A condition preferable to culture the cell in a liquid medium or a solid medium may be selected. For example, when an animal cell is selected, a medium such as DMEM, MEM, RPMI1640, IMDM or the like may be used. When necessary, serum such as fetal calf serum (FCS) or the like, amino acid, glucose, penicillin, streptomycin or the like may be added. Culturing may be performed at a pH value of about 6 to 8 and 30 to 40° C. for 15 to 200 hours. When necessary, the medium may be changed, or ventilation or stirring may be performed.

A cell containing the group of proteins metabolically isotope-labeled thus obtained is crushed, and thus a group of isotope-labeled proteins can be prepared. Usable methods for crushing include methods using a Dounce-type Teflon™ homogenizer, a polytron, a Waring blender, a Potter-type glass homogenizer, an ultrasonic crushing device, a cell-dissolved solution (e.g., M-PER: Cat. No. 78501; T-PER: Cat. No. 78510; both by PIERCE, etc.) and the like, and a freezing and thawing method. A method using a cell-dissolved solution is preferable. The crushed cell is preferably deprived of insoluble substances by centrifugation. In this way, the group of isotope-labeled proteins can be prepared.

An isotope used in the present invention may be a radioactive isotope, but a stable isotope with no radioactivity is easy to handle and especially preferable. Usable stable isotopes include, for example, $^2H$, $^{13}C$, $^{15}N$, $^{17}O$, $^{18}O$, $^{31}P$, $^{34}S$ or a combination thereof. $^2H$, $^{13}C$, $^{15}N$, $^{18}O$ or a combination thereof is preferable; $^{13}C$, $^{15}N$, $^{18}O$ or a combination thereof is more preferable; and $^{13}C$ is still more preferable. According to the present invention, any type of isotope which can label a protein is usable with no specific limitation. Specifically, $^{13}C$ label ($^{13}C\times 6$) leucine (produced by Cambridge Isotope Labs (CIL), L-Leucine U—$^{13}C6$, CLM-2262) is usable as a precursor of an isotope-labeled protein. The above-mentioned isotopes are applicable to all the embodiments of the present invention.

The group of isotope-labeled proteins may also be prepared in vitro. For example, the proteins may be isotope-labeled by alkylating cysteine residue in the proteins using an isotope-labeled alkylating reagent (see Rapid Communications in Mass Spectroscopy, Vol. 16, No. 15 (2002), pp. 1416-1424). Alternatively, the proteins may be isotope-labeled by biotinylating cysteine residue in the proteins using an isotope-labeled biotinylating reagent. After the labeling, only the labeled proteins may be purified using an avidin column (Nature Biotechnology, Vol. 17, No. 10, October 1999, pp. 994-999).

Alternatively, the group of isotope-labeled proteins may be prepared by chemical synthesis.

The group of isotope-labeled proteins may be preliminary fractionated. Usable preliminary fractionation methods include, for example, differential centrifugation, sucrose density gradient centrifugation, and the like. Sucrose density gradient centrifugation is preferable.

Optionally, the group of isotope-labeled proteins may be separated. Usable separation methods include, for example, electrophoresis (e.g., two-dimensional electrophoresis, SDS-PAGE, etc.), methods using group-specific affinity chromatography, cation exchange chromatography, anion exchange chromatography and reverse phase chromatography, immunoprecipitation, ammonium sulfate precipitation, precipitation by an organic solvent, ultrafiltration, gel filtration, dialysis, and the like. A method using reverse phase chromatography is preferable.

The group of isotope-labeled proteins may be stored under an appropriate condition, preferably at −20° C. or lower, especially preferably at −80° C. or lower.

In the present invention, the expression "carrier having a compound immobilized thereon" refers to a carrier having a compound covalently or noncovalently bound thereto via a functional group.

A carrier having the compound immobilized thereon is obtained, for example, as follows. First, N-hydroxy-succinimide or hydrazide as a functional group is covalently bound to the carrier; simply an amino group is formed to the carrier; or Protein A, heparin, Cibacron Blue F3GA or the like is immobilized on the carrier. Then, a compound is covalently or noncovalently bound to such a carrier, with or without the structure of the compound being partially changed.

There is no specific limitation on the compound to be immobilized on the carrier. Usable compounds include, for example, synthesized compounds having a low molecular weight, proteins, synthesized peptides, purified or partially purified polypeptides, antibodies, cell released substances (encompassing cell metabolic products), intra-biological cellular nucleic acid substances (e.g., ATP, GTP, NAD/NADH, NADP/NADPH, etc.), and lipid.

Such a compound may be a novel compound or a known compound. Usable carriers include, for example, agarose gel, acrylamide, magnetic bead, cellulose, silica gel, and the like. Agarose gel is preferable. Such a carrier is available from, for example, BioRad (Affi-gel, produced by BioRad, Cat. No. 153-6099).

A carrier having a compound immobilized thereon may be produced by binding a desired compound to the carrier. A carrier having, for example, a compound containing an amino group immobilized thereon may be produced as follows. First, a compound solution containing an amino group is added to a carrier having N-hydroxy-succinimide binding thereto (e.g., Affi-gel 10). Next, triethylamine is added thereto and incubated. Then, 2-aminoethanol is added thereto and further incubated. Thus, a carrier having a compound containing an amino group immobilized thereon is produced. It is preferable to perform a washing operation when necessary.

A carrier having a compound containing, for example, carboxylic acid immobilized thereon may be produced as follows. First, carbodiamide is added to a compound solution containing carboxylic acid, and incubated. The resultant substance is added to a carrier having an amino acid binding thereto. Next, acetic acid (or lactic acid) is added and further incubated. Thus, a carrier having a compound containing carboxylic acid immobilized thereon is produced. It is preferable to perform a washing operation when necessary. A carrier having an NADP analog immobilized thereon is available from, for example, Amersham Biosciences (2'5' ADP Sepharose 4B (code number: 17-0700-01)).

A carrier having a compound containing a thiol group immobilized thereon may be produced using, for example, SulfoLink (PIERCE, Cat. No. 44895). A carrier having a compound containing an aldehyde group immobilized thereon may be produced using, for example, CarboLink (PIERCE, Cat. No. 44900).

A carrier having a compound containing a hydroxyl group such as sugar immobilized thereon may be produced using CarboLink (PIERCE, Cat. No. 44900) or the like, because an aldehyde group can be generated from the hydroxyl group of the compound by, for example, oxidation performed with 10 mM periodic acid at room temperature. A compound having an active hydrogen atom (exchangeable hydrogen atom) (an example of such a compound is estradiol 17β having a cholesterol backbone) can be immobilized on a carrier by causing concentration by Mannich reaction among three substances of the compound, formaldehyde, and the amino group immobilized on the carrier.

There is no specific limitation on the amount of the compound to be immobilized on the carrier. A preferable amount is 0.1 mg to several milligrams with respect to 1 ml of the carrier.

A carrier having a compound immobilized thereon is usable for affinity chromatography. When an appropriate column (e.g., Polyprep empty column (produced by BioRad, Cat. No. 731-1550), etc.) is filled with such a carrier, the carrier is usable as an affinity chromatography column having a compound immobilized thereon. Such a carrier having a compound immobilized thereon is also usable when being put into an appropriate tube (e.g., Eppendorf tube (produced by Eppendorf), etc.).

The group of isotope-labeled proteins are fractionated into plural fractions using a carrier having a compound immobilized thereon. By this, plural kinds of proteins bound to the compound immobilized on the carrier can be fractionated to obtain fractions. As used herein, the expression "using a carrier" refers to using a carrier having a compound immobilized thereon when fractionating the group of proteins as a population.

Hereinafter, this will be described in detail.

First, a carrier having a compound immobilized thereon is equilibrated with an appropriate solution. There is no specific limitation on the solution for equilibration, but a solution which can dissolve proteins and does not denature the proteins is preferable. For example, a phosphoric acid buffer solution, a Hepes buffer solution, or Tris buffer solution, each prepared to have a physiological pH value, is usable. When necessary, sodium chloride and/or a surfactant (e.g., n-octylglucoside) may be added thereto in an appropriate amount.

In the case where an appropriate column is filled with the carrier having the compound immobilized thereon, the step of equilibration may be performed by applying an appropriate solution to the column. In the case where the carrier having the compound immobilized thereon is put to an appropriate tube, the step of equilibration may be performed by applying an appropriate solution to the tube.

Next, the group of isotope-labeled proteins, and the carrier having the compound immobilized thereon, are put into contact with each other. In the case where an appropriate column is filled with the carrier having the compound immobilized thereon, the step of putting the group of isotope-labeled proteins, and the carrier having the compound immobilized thereon, into contact with each other may be performed by loading the group of isotope-labeled proteins to the column. In the case where the carrier having the compound immobilized thereon is put to an appropriate tube, the above-mentioned step may be performed by adding the group of isotope-labeled proteins to the tube.

Then, desirably, the carrier having a compound immobilized thereon is washed with an appropriate solution. In the case where an appropriate column is filled with the carrier having the compound immobilized thereon, the washing operation may be performed by adding an appropriate solution to the column. In the case where the carrier having the compound immobilized thereon is put to an appropriate tube, the washing operation may be performed by adding an appropriate solution to the tube and conducting a centrifugal operation.

Then, the group of isotope-labeled proteins are eluted with an appropriate solution.

The samples may be eluted while changing the strength of the eluting solvent. The "strength" is also referred to as the "eluting power", and means a chemical strength for eluting a sample bound to a column. The strength is influenced by the concentration of the eluting solvent or the like. Accordingly, "changing the strength of the eluting solvent" means, for example, applying a concentration gradient of the solvent continuously or incontinuously. Elution may be performed by a method of denaturing the samples bound to the column with guanidine hydrochloride, urea or the like, a method of changing the salt concentration with KCl, NaCl or the like, a method of changing the pH value, or the like.

Chemically bound samples may be eluted by adding an excessive amount of a compound having the same or a similar backbone to that of the compound immobilized on the carrier.

In the case where an appropriate column is filled with the carrier having the compound immobilized thereon, the step of eluting the group of isotope-labeled proteins may be performed by loading an appropriate solution to the column. In the case where the carrier having the compound immobilized thereon is put to an appropriate tube, the step of eluting the group of isotope-labeled proteins may be performed by applying an appropriate solution to the tube and performing centrifugation.

By these methods, the group of proteins bound to the carrier having the compound immobilized thereon can be fractionated to obtain fractions.

The temperature for the above-described operation is not specifically limited, but is preferably 4° C. to 37° C., and more preferably 4° C. to 20° C.

(b) the Step of Fractionating a Second Group of Proteins into One or Plural Fractions Using a Carrier Having the Compound Immobilized Thereon In this step, the second group of proteins are samples for the internal standard fraction.

In this step, separately from step (a) above, the same samples (second group of proteins) which are not isotope-labeled are fractionated into one or plural fractions using the carrier having the compound immobilized thereon. In the first embodiment of the present invention, the fractions of the group of isotope-labeled proteins are used as the test target (target of analysis), and the fractions of the group of non-isotope-labeled proteins are used as the internal standard fraction. The internal standard fraction means a fraction acting as a standard in a measurement system.

As used herein, the term "group of non-isotope-labeled proteins" refers to an assembly comprising proteins on which the act of isotope labeling is not conducted.

As the group of non-isotope-labeled proteins (the second group of proteins in the first embodiment), samples obtained from, for example, tissues, bodily fluids from living organisms, cells, cell organella, protein composites and the like are usable.

Usable methods for crushing include be methods using a Dounce-type Teflon™ homogenizer, a polytron, a Waring blender, a Potter-type glass homogenizer, an ultrasonic crushing device, a cell-dissolved solution (e.g., M-PER: Cat. No. 78501; T-PER: Cat. No. 78510; both by PIERCE, etc.) and the like, and a freezing and thawing method. A method using a cell-dissolved solution is preferable. The crushed cell is preferably deprived of insoluble substances by centrifugation. In this way, the group of non-isotope-labeled proteins can be prepared.

Alternatively, the group of non-isotope-labeled proteins may be prepared by chemical synthesis.

The group of non-isotope-labeled proteins may be stored under an appropriate condition, preferably at −20° C. or lower, especially preferably at −80° C. or lower.

In the present invention, the "group of non-isotope-labeled proteins" are preferably prepared by the same method as the "group of isotope-labeled proteins" using a naturally-occurring reagent (non-isotope reagent).

According to the present invention, instead of the "group of non-isotope-labeled proteins", a group of proteins labeled with an isotope different from the isotope in the "group of isotope-labeled proteins" (hereinafter, referred to also as a "group of different-isotope-labeled proteins") are usable. The isotope in the "group of different-isotope-labeled proteins" may be different from the isotope in the "group of isotope-labeled proteins" or may include the same isotope, as long as the proteins can be labeled such that proteins derived from these groups of proteins and corresponding to each other have different masses.

The group of non-isotope-labeled proteins may be preferably fractionated using the same carrier as that used in step (a). By this, plural kinds of proteins bound to the compound immobilized on the carrier can be fractionated to obtain fractions.

The samples may be eluted while changing the strength of the eluting solvent, or at a constant eluting power without changing the strength of the eluting solvent. In step (b) of fractionating a second group of proteins into one or plural fractions using a carrier having the compound immobilized thereon, the same eluting condition as that of step (a) is desirably selected. In this specification, the number of fractions obtained by fractionating the samples for the internal standard fraction may be one as described in the example provided later.

(c) the Step of Adding a Certain Amount of the One Fraction Obtained in Step (b), or a Certain Amount of a Mixture of all the Fractions or a Mixture of Plural Contiguous Fractions Among the Fractions Obtained in Step (b), to Each of the Fractions Obtained in Step (a)

In this step, the internal standard fraction is added to each of the fractions obtained by fractionating the group of isotope-labeled proteins using the carrier having the compound immobilized thereon. The term "addition" means mixing fractions.

In this step, the internal standard fraction means the "one fraction obtained in step (b)", or the "mixture of all the fractions" or the "mixture of plural contiguous fractions" among the fractions obtained in step (b). The "one fraction obtained in step (b)" means the obtained fraction when one fraction is obtained by the fractionation in step (b). The "mixture of all the fractions" means a mixture of all the eluted fractions or a mixture of a certain amount of each of all the eluted fractions. The "mixture of plural contiguous fractions" means a mixture of a series of plural contiguous fractions or a mixture of a certain amount of each of such plural contiguous fractions.

According to the present invention, the protein samples for the internal standard fraction may be fractionated in substantially the same manner as the test protein samples (FIG. 2, $a_1$) to obtain five fractions (FIG. 2, $a_2$) as follows, for example. FIG. 2 shows an example of elution in affinity purification. The fractions are respectively referred to as fractions 1 through 5. The "plural contiguous fractions" means an assembly comprising a series of contiguous fractions, for example, fractions 1 and 2, fractions 2 and 3, fractions 3 through 5, or the like. The "certain amount" may be arbitrarily set in accordance with the purpose, and is preferably set such that the amounts to be added to the fractions (for example, fractions 1 through 5 in FIG. 2, b) are equal. In the case where the samples for the internal standard fraction are fractionated to obtain one fraction (FIG. 2, $a_{2'}$) also, it is preferable that the amounts to be added to the fractions (for example, fractions 1 through 5 in FIG. 2, b) are equal.

(d) The Step of Analyzing the Fractions Obtained in Step (c) with Mass Spectrometry In this step, the fractions obtained in step (c), namely, the mixture samples obtained after the internal standard fraction is added to the isotope-labeled fractions are analyzed with mass spectrometry.

The mixture samples may be analyzed with mass spectrometry as they are or may be pre-treated with concentration, separation or the like. A usable method for concentration uses, for example, Amicon Ultra-15 10,000MWCO or the like. Usable methods for separation include, for example, electrophoresis (e.g., two-dimensional electrophoresis, SDS-PAGE, etc.), various types of chromatography (e.g., affinity chromatography, reverse phase chromatography, anion exchange chromatography, cation exchange chromatography, etc.), and the like.

The mixture samples may also be digested. Usable methods for digestion include enzymatic digestion, chemical decomposition and the like. Enzymatic digestion is preferable. Enzymes usable for enzymatic digestion include trypsin, chymotrypsin, Lys-C, Asp-N, Glu-C and the like. Trypsin is preferable. For enzymatic digestion, it is desirable to add a surfactant, preferably, 5-cyclohexyl-pentyl-beta-D-maltoside (U.S. Pat. No. 5,674,987 and U.S. Pat. No. 5,763, 586, Anatrace Inc., Maumee, Ohio, USA).

Usable spectrometry devices include general-purpose devices such as a gas chromatography mass spectrometry (GC/MS) device, which is a mass spectrometry device combined with a gas chromatography device, a liquid chromatography mass spectrometry (LC/MS) device, which is a mass spectrometry device combined with a liquid chromatography device, and the like. Ionization methods usable by a mass spectrometry device include, for example, MALDI (matrix-assisted laser desorption/ionization), ESI (electrospray ionization), EI (electron impact ionization), CI (chemical ionization), APCI (atmospheric pressure chemical ionization), FAB (fast atom bombardment), LD, FD, SIMS, TSP and the like. MALDI and ESI are preferable. Usable analyzers include, for example, devices of TOF (time of flight) type, ion trap type, double-focusing type, quadruple pole type, Fourier transformation type and the like.

As the mass spectrometry device, a device having two mass spectrometers connected in series (MS/MS) is preferable.

A mass spectrum is obtained by the measurement performed by the mass spectrometry device. From the mass spectrum, information on the peaks derived from proteins (or peptides) can be obtained.

By checking the data obtained by the measurement performed by the mass spectrometry device against protein database using software, the proteins in the samples can be identified. Examples of the software include SonarMSMS (produced by Genomic Solution), MASCOT (produced by Matrix Science), The Global Proteome Machine (GPM; The Global Proteome Machine Organization, http://h451.thegpm.org/tandem/thegpm_tandem.html), and the like. Usable databases include, for example, NCBInr (http://www.ncbi.nlm.nih.gov/), IPI, Sprot and the like. By checking the data obtained by the measurement performed by the mass spectrometry device against protein database, the proteins can be identified (Nat Genet. 1998: 20, 46-50; J Cell Biol. 1998: 141, 967-977; J Cell Biol. 2000: 148, 635-651; Nature. 2002: 415, 141-147; Nature. 2002: 415, 180-183; Curr Opin Cell Biol. 2003: 15, 199-205; Curr Opin Cell Biol. 2003: 7, 21-27). Based on the information on the identified proteins, amino acid sequence information can be obtained.

(e) The Step of, Based on the Mass Spectrometry Information, Obtaining, Regarding Each Fraction, an Intensity Ratio Between a Peak Derived from a Protein in the Fraction Obtained in Step (a) and a Peak Derived from a Protein in the Fraction Obtained in Step (b), and Comparing Degrees of the Binding Ability of the Plural Kinds of Proteins to the Compound In the present invention, the "peak derived from a protein in the fraction obtained in step (a)" refers to each of signal strengths derived from the test protein sample or a total thereof (usually represented with an area as understood by those skilled in the art) in the mass spectrum obtained by the measurement performed by the mass spectrometry device (hereinafter, such a peak may be occasionally referred to simply as the "test fraction peak" for the convenience of explanation).

The "peak derived from a protein in the fraction obtained in step (b)" refers to each of signal strengths derived from the internal standard fraction or a total thereof in the mass spectrum obtained by the measurement performed by the mass spectrometry device (hereinafter, such a peak may be occasionally referred to simply as the "internal standard peak" for the convenience of explanation).

Using the data obtained by the measurement performed by the mass spectrometry, the intensity ratio between the test fraction peak and the internal standard peak (="intensity of the test fraction peak"/"intensity of the internal standard peak; hereinafter, occasionally referred to simply as the "peak intensity ratio") is found for each protein. By this, the degrees of the binding ability of the plural kinds of proteins to the compound can be compared. As used herein, the expression "compare the degrees of the binding ability of the plural kinds of proteins to the compound" means to find in which fraction each protein is most concentrated, using the peak intensity ratios of the plural kinds of proteins, and thus to compare the binding ability to the compound among the proteins.

An isotope-labeled protein has a larger molecular weight than a non-isotope-labeled protein by the difference of the isotope-labeled molecules, and the isotope-labeled protein and the non-isotope-labeled protein are observed as a pair of peaks on the mass spectrum (FIG. 2, c). In the case where the mass spectrometry is conducted on groups of proteins labeled with different isotopes, these groups of proteins are observed as a pair of peaks. The molecular weight of the isotope-labeled protein can be obtained by calculation based on the identified protein and the amino acid sequence thereof. In the case where a protein is eluted in plural fractions, the protein is eluted while being most concentrated in the fraction having the largest peak intensity ratio. Regarding each fraction, the protein having the largest peak intensity ratio can be determined to be most concentrated in that fraction. A protein concentrated in a fraction eluted later (fraction eluted with a stronger eluting solvent) can be determined to have a higher binding ability to the compound immobilized to the carrier.

(2) Second Embodiment

A second embodiment of the present invention comprises the following steps for analyzing a binding ability of protein to a compound, wherein samples for the internal standard fraction are isotope-labeled before fractionation:
 (a) step of fractionating a first group of proteins into plural fractions using a carrier having the compound immobilized thereon;
 (b) step of fractionating a second group of isotope-labeled proteins into one or plural fractions using a carrier having the compound immobilized thereon;
 (c) step of adding a certain amount of the one fraction obtained in step (b), or a certain amount of a mixture of all the fractions or a mixture of plural contiguous fractions among the fractions obtained in step (b), to each of the fractions obtained in step (a);
 (d) step of analyzing the fractions obtained in step (c) with mass spectrometry; and
 (e) step of, based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

In the second embodiment of the method of the present invention, the group of proteins are isotope-labeled before being fractionated like in the first embodiment. In the first embodiment, the first group of proteins as the test samples are isotope-labeled; whereas in the second embodiment, the second group of proteins for the internal standard fraction are isotope-labeled. In the second embodiment, the other steps are the same as in the first embodiment. It should be noted that the first group of proteins may be labeled with an isotope different from the isotope used for labeling the second group of proteins.

(3) Third Embodiment

A third embodiment of the present invention is directed to a method for analyzing a binding ability of protein to a compound, comprising the following steps, wherein test protein samples are labeled after fractionation:
 (a) step of fractionating a first group of proteins into plural fractions using a carrier having the compound immobilized thereon;
 (b) step of fractionating a second group of proteins into one or plural fractions using a carrier having the compound immobilized thereon;
 (c) step of labeling the fractions obtained in step (a);
 (d) step of adding a certain amount of the one fraction obtained in step (b), or a certain amount of a mixture of all the fractions or a mixture of plural contiguous fractions among the fractions obtained in step (b), to each of the fractions labeled in step (c);

(e) step of analyzing the fractions obtained in step (d) with mass spectrometry; and (f) step of, based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

In the third embodiment, after the first group of proteins as the target of analysis are fractionated, the post-fractionation fractions (test fractions) are labeled. Namely, the fractions after being fractionated in FIG. 2, $a_1$ (fractions 1 through 5 in FIG. 2, $a_1$) are labeled. Except for this, the third embodiment is substantially the same as the first embodiment.

Any labeling is usable as long as a protein derived from the first group of proteins and the same type of protein derived from the second group of proteins are distinguishable in mass spectrometry. Usable methods for labeling include, for example, methylation, ethylation, biotinylation and a combination thereof in addition to isotope labeling in the above-described embodiments. Those skilled in the art would carry out such labeling of proteins using known methods.

The first group of proteins and the second group of proteins may be labeled with different isotopes, or labeled with different labeling substances.

(4) Fourth Embodiment

A fourth embodiment of the present invention is directed to a method for analyzing a binding ability of protein to a compound, comprising the following steps, wherein the samples for the internal standard fraction are fractionated and the post-fractionation fractions for the internal standard fraction are labeled:

(a) step of fractionating a first group of proteins into plural fractions using a carrier having the compound immobilized thereon;

(b) step of fractionating a second group of proteins into one or plural fractions using a carrier having the compound immobilized thereon;

(c) step of labeling the one fraction obtained in step (b), or a mixture of all the fractions or a mixture of plural contiguous fractions among the fractions obtained in step (b);

(d) step of adding a certain amount of the fraction or the mixture labeled in step (c) to each of the fractions obtained in step (a);

(e) step of analyzing the fractions obtained in step (d) with mass spectrometry; and (f) step of, based on the mass spectrometry information, obtaining, regarding each fraction, an intensity ratio between a peak derived from a protein in the fraction obtained in step (a) and a peak derived from a protein in the fraction obtained in step (b), and comparing degrees of the binding ability of the plural kinds of proteins to the compound.

In the fourth embodiment, the protein samples for the internal standard fraction are fractionated and then a mixture of all the fractions eluted or a mixture of plural contiguous fractions eluted is entirely labeled. The mixture of fractions is as described above in the section of "1. Overview of the present invention" or "First embodiment". It should be noted that in step (c), it is not necessary to label all the fractions (for example, fractions 1 through 5 in FIG. 2), and a certain amount of each fraction may be sampled and the sampled fractions may be labeled. Alternatively, the elution may be performed such that one fraction would be obtained by fractionation and the entire amount or a certain amount of that fraction may be labeled. A mixture of the fractions may be labeled, or each of the fractions may be labeled before being mixed.

Any labeling is usable as long as a protein derived from the first group of proteins and the same type of protein derived from the second group of proteins are distinguishable in mass spectrometry. Usable methods for labeling include, for example, methylation, ethylation, biotinylation and a combination thereof in addition to isotope labeling in the above-described embodiments. Those skilled in the art would carry out such labeling of proteins using known methods. In this embodiment also, the first group of proteins and the second group of proteins may be labeled with different isotopes, or labeled with different labeling substances.

(5) Fifth Embodiment

A fifth embodiment of the present invention is directed to a method for analyzing a binding ability of protein to a compound, comprising the following steps, wherein the test protein samples and the samples for the internal standard fraction are fractionated and then quantitated:

(a1) step of fractionating a first group of proteins into plural fractions using a carrier having the compound immobilized thereon;

(a2) step of analyzing the fractions obtained in step (a1) with mass spectrometry;

(a3) step of identifying each of the proteins in the fractions obtained in step (a1) based on the mass spectrometry information obtained in step (a2);

(a4) step of quantitating each of the proteins in the fractions obtained in step (a1);

(b1) step of fractionating a second group of proteins into one or plural fractions using a carrier having the compound immobilized thereon;

(b2) step of analyzing the one fraction obtained in step (b1), or a mixture of all the fractions or a mixture of plural contiguous fractions among the fractions obtained in step (b1), with mass spectrometry;

(b3) step of identifying each of the proteins in the one fraction or the mixture recited in step (b2) based on the mass spectrometry information obtained in step (b2);

(b4) step of quantitating each of the proteins in the one fraction or the mixture recited in step (b2); and (c) step of obtaining, regarding each fraction obtained in step (a1), a ratio between the protein quantity obtained in step (a4) and the protein quantity obtained in step (b4), and comparing degrees of the binding ability of the plural kinds of proteins to the compound.

In the fifth embodiment, the first group of proteins as the target of analysis are fractionated, and then the post-fractionation fractions (test fractions) are quantitated. The protein samples for the internal standard fraction are fractionated, and then a mixture of all the fractions eluted or a mixture of plural contiguous fractions eluted is formed and the mixture is entirely quantitated.

Hereinafter, the fifth embodiment will be described in detail.

(a1) The Step of Fractionating a First Group of Proteins into Plural Fractions Using a Carrier Having the Compound Immobilized Thereon This step can be performed by substantially the same manner as "(a) the step of fractionating a first group of isotope-labeled proteins into plural fractions using a carrier having the compound immobilized thereon" in the first embodiment. It should be noted that the first group of proteins do not need to be isotope-labeled.

(a2) The Step of Analyzing the Fractions Obtained in Step (a1) with Mass Spectrometry This step can be performed by substantially the same manner as "(d) the step of analyzing the fractions obtained in step (c) with mass spectrometry" in the first embodiment.

(a3) The Step of Identifying Each of the Proteins in the Fractions Obtained in Step (a1) Based on the Mass Spectrometry Information Obtained in Step (a2)

This step can be performed by the manner described regarding "(d) the step of analyzing the fractions obtained in step (c) with mass spectrometry" in the first embodiment.

(a4) The Step of Quantitating Each of the Proteins in the Fractions Obtained in Step (a1)

In this step, there is no specific limitation on the method for quantitating each protein. For example, the proteins can be quantitated as follows.

Regarding the proteins identified in step (a3), the number of detected peptides ($N_{obsd}$) and the number of detectable peptides ($N_{obsbl}$) are calculated.

The "number of detected peptides ($N_{obsd}$)" refers to the number of peptides actually detected in "(a2) the step of analyzing the fractions obtained in step (a1) with mass spectrometry". The number of detected peptides ($N_{obsd}$) may be calculated based on the mass spectrometry data and sequence information of the identified proteins. When calculated based on the mass spectrometry data, the number of detected peptides ($N_{obsd}$) matches the number of peaks detected in mass spectrometry for each protein.

The "number of detectable peptides ($N_{obsbl}$)" refers to the number of peptides which can be theoretically detected in "(a2) the step of analyzing the fractions obtained in step (a1) with mass spectrometry". The number of detectable peptides ($N_{obsbl}$) may be calculated based on the sequence information of the identified proteins. Regarding each protein, the number of peptides theoretically generated by the concentration, separation (e.g., HPLC separation), digestion or other operations in the above-described steps is calculated based on the sequence information, and thus the number of peptides detectable by mass spectrometry ($N_{obsbl}$) can be obtained. For example, when mass spectrometry is performed on the samples treated with digestion with trypsin, the peptide chains are cut by trypsin on the carboxyl side of lysine and arginine. Therefore, the number of peptides generated by the cutting can be predicted based on the sequence information of each protein. In some cases, the number of detectable peptides ($N_{obsbl}$) may be obtained in consideration of the measurement range of the mass spectrometer.

Next, in order to quantitate each protein using the number of detectable peptides ($N_{obsbl}$) and the number of detected peptides ($N_{obsd}$), EMPAI (exponentially modified protein abundance index) is set in accordance with expression (I).

$$EMPAI = 10^{N_{obsd}/N_{obsbl}} - 1 \quad \text{Expression (I)}$$

EMPAI is an index in proportion to the protein content in a protein mixture.

Then, the protein content (mol %) may be calculated in accordance with expression (II).

$$\text{Protein content(mol \%)} = \frac{EMPAI}{\sum(EMPAI)} \times 100 \quad \text{Expression (II)}$$

In the expression, $\Sigma(EMPAI)$ represents a sum of EMPAIs of all the identified proteins.

The protein content (wt. %) may be calculated in accordance with expression (III).

$$\text{Protein content(wt. \%)} = \frac{EMPAI \times MW}{\sum(EMPAI \times MW)} \times 100 \quad \text{Expression (III)}$$

In the expression, MW represents the molecular weight of each identified protein. $\Sigma(EMPAI \times MW)$ represents the sum of the EMPAI×MW values of all the identified proteins.

The molecular weight of each protein may be calculated from the amino acid sequence. The total weight of the proteins in the fractions obtained in step (a1) may be easily measured by a known method, for example, the Lowry method, the Bradford method, absorbance measurement at 280 nm or the like. Based on the total weight of the proteins in the fractions obtained in step (a1) and the above-obtained protein content, each protein can be quantitated.

Thus, each protein can be quantitated by the above-described method.

The step of quantitating each protein may be performed using a computer.

(b1) the Step of Fractionating a Second Group of Proteins into One or Plural Fractions Using a Carrier Having the Compound Immobilized Thereon This step can be performed by substantially the same manner as "(b) fractionating a second group of proteins into one or plural fractions using a carrier having the compound immobilized thereon" in the first embodiment.

(b2) The Step of Analyzing the One Fraction Obtained in Step (b1), or a Mixture of all the Fractions or a Mixture of Plural Contiguous Fractions Among the Fractions Obtained in Step (b1), with Mass Spectrometry In this step, the "one fraction obtained in step (b1)", the "mixture of all the fractions", and the "mixture of plural contiguous fractions" are as described regarding the "one fraction obtained in step (b)", the "mixture of all the fractions", and the "mixture of plural contiguous fractions" in the section of the "First embodiment". This step can be performed by substantially the same manner as "(d) analyzing the fractions obtained in step (c) with mass spectrometry" in the first embodiment.

(b3) The Step of Identifying Each of the Proteins in the One Fraction or the Mixture Recited in Step (b1) Based on the Mass Spectrometry Information Obtained in Step (b2)

This step can be performed by the manner described regarding "(d) analyzing the fractions obtained in step (c) with mass spectrometry" in the first embodiment.

(b4) The Step of Quantitating Each of the Proteins in the One Fraction or the Mixture Recited in Step (b2)

This step can be performed by substantially the same manner as "(a4) quantitating each of the proteins in the fractions obtained in step (a1)" above.

(c) the Step of Obtaining, Regarding Each Fraction Obtained in Step (a1), a Ratio Between the Protein Quantity Obtained in Step (a4) and the Protein Quantity Obtained in Step (b4), and Comparing Degrees of the Binding Ability of the Plural Kinds of Proteins to the Compound In this step, regarding each of the proteins identified in step (a3) and each of the proteins identified in step (b3), the ratio between the protein quantity in each fraction obtained in step (a1) and the protein quantity in the one fraction or the mixture recited in step (b2) (="protein quantity obtained in step (a4)"/"protein quantity obtained in step (b4)" is found. By this, the degrees of the binding ability of the plural kinds of proteins to the compound can be compared.

Namely, in the fifth embodiment of finding the protein quantity ratio, in the case where a protein is eluted in plural fractions obtained in step (a1), the protein is eluted while being most concentrated in the fraction having the largest protein quantity ratio. Regarding each fraction, the protein having the largest protein quantity ratio can be determined to be most concentrated in that fraction. A protein concentrated in a fraction eluted later (fraction eluted with a stronger eluting solvent) can be determined to have a higher binding ability to the compound immobilized to the carrier.

The method in the fifth embodiment is characterized in that it is not necessary to label each protein with an isotope.

(6) Sixth Embodiment

A sixth embodiment of the present invention is directed to a method for analyzing a binding ability of protein to a compound, comprising the following steps, wherein the test protein samples and the samples for the internal standard fraction are fractionated and then the EMPAI of each protein is calculated:
  (a1) step of fractionating a first group of proteins into plural fractions using a carrier having the compound immobilized thereon;
  (a2) step of analyzing the fractions obtained in step (a1) with mass spectrometry;
  (a3) step of identifying each of the proteins in the fractions obtained in step (a1) based on the mass spectrometry information obtained in step (a2);
  (a4) step of calculating an EMPAI of each of the proteins in the fractions obtained in step (a1);
  (b1) step of fractionating a second group of proteins into one or plural fractions using a carrier having the compound immobilized thereon;
  (b2) step of analyzing the one fraction obtained in step (b1), or a mixture of all the fractions or a mixture of plural contiguous fractions among the fractions obtained in step (b1), with mass spectrometry;
  (b3) step of identifying each of the proteins in the one fraction or the mixture recited in step (b2) based on the mass spectrometry information obtained in step (b2);
  (b4) step of calculating an EMPAI of each of the proteins in the one fraction or the mixture recited in step (b2); and
  (c) step of obtaining, regarding each fraction obtained in step (a1), a ratio between the EMPAI obtained in step (a4) and the EMPAI obtained in step (b4), and comparing degrees of the binding ability of the plural kinds of proteins to the compound.

As described above, EMPAI is an index in proportion to the protein content in a protein mixture. Therefore, by finding, regarding each of the proteins identified in step (a3) and step (b3), the ratio between the EMPAI of a protein in each fraction obtained in step (a1) and the EMPAI of a protein in the one fraction or the mixture recited in step (b2) (="EMPAI obtained in step (a4)"/"EMPAI obtained in step (b4)", the degrees of the binding ability of the plural kinds of proteins to the compound can be compared.

Namely, in the sixth embodiment of finding the EMPAI ratio, in the case where a protein is eluted in plural fractions, the protein is eluted while being most concentrated in the fraction having the largest EMPAI ratio. Regarding each fraction, the protein having the largest EMPAI ratio can be determined to be most concentrated in that fraction. A protein concentrated in a fraction eluted later can be determined to have a higher binding ability to the compound immobilized to the carrier.

As described above, in the first through sixth embodiments of the method for analysis of the present invention, the samples for the internal standard fraction are fractionated using a carrier having a compound immobilized thereon. Embodiments in which the samples for the internal standard fraction are used without being fractionated using a carrier having a compound immobilized thereon are also encompassed in the present invention.

(7) Seventh Embodiment

A seventh embodiment of the present invention comprises the following steps for analyzing a binding ability of protein to a compound:
  (a) step of fractionating a first group of isotope-labeled proteins into plural fractions using a carrier having the compound immobilized thereon;
  (b) step of adding a certain amount of a second group of proteins to each of the fractions obtained in step (a);
  (c) step of analyzing the fractions obtained in step (b) with mass spectrometry; and
  (d) step of, based on the mass spectrometry information, obtaining, regarding each fraction, an intensity ratio between a peak derived from a protein in the fraction obtained in step (a) and a peak derived from a protein in the second group of proteins, and comparing degrees of the binding ability of the plural kinds of proteins to the compound.

In the seventh embodiment, unlike in the first embodiment, the second group of proteins for the internal standard fraction are added in a certain amount to each of the fractions obtained in step (a) without being fractionated into one or plural fractions using the carrier having the compound immobilized thereon. Except for this, the seventh embodiment is substantially the same as the first embodiment.

(8) Eighth Embodiment

An eighth embodiment of the present invention comprises the following steps for analyzing a binding ability of protein to a compound:
  (a) step of fractionating a first group of proteins into plural fractions using a carrier having the compound immobilized thereon;
  (b) step of adding a certain amount of a second group of isotope-labeled proteins to each of the fractions obtained in step (a);
  (c) step of analyzing the fractions obtained in step (b) with mass spectrometry; and
  (d) step of, based on the mass spectrometry information, obtaining, regarding each fraction, an intensity ratio between a peak derived from a protein in the fraction obtained in step (a) and a peak derived from a protein in the second group of proteins, and comparing degrees of the binding ability of the plural kinds of proteins to the compound.

In the eighth embodiment, unlike in the second embodiment, the second group of isotope-labeled proteins for the internal standard fraction are added in a certain amount to each of the fractions obtained in step (a) without being fractionated into one or plural fractions using the carrier having the compound immobilized thereon. Except for this, the eighth embodiment is substantially the same as the second embodiment.

(9) Ninth Embodiment

A ninth embodiment of the present invention comprises the following steps for analyzing a binding ability of protein to a compound:
- (a) step of fractionating a first group of proteins into plural fractions using a carrier having the compound immobilized thereon;
- (b) step of labeling the fractions obtained in step (a);
- (c) step of adding a certain amount of a second group of proteins to each of the fractions labeled in step (b);
- (d) step of analyzing the fractions obtained in step (c) with mass spectrometry; and
- (e) step of, based on the mass spectrometry information, obtaining, regarding each fraction, an intensity ratio between a peak derived from a protein in the fraction obtained in step (a) and a peak derived from a protein in the second group of proteins, and comparing degrees of the binding ability of the plural kinds of proteins to the compound.

In the ninth embodiment, unlike in the third embodiment, the second group of proteins for the internal standard fraction are added in a certain amount to each of the fractions obtained in step (b) without being fractionated into one or plural fractions using the carrier having the compound immobilized thereon. Except for this, the ninth embodiment is substantially the same as the third embodiment.

(10) Tenth Embodiment

A tenth embodiment of the present invention comprises the following steps for analyzing a binding ability of protein to a compound:
- (a1) step of fractionating a first group of proteins into plural fractions using a carrier having the compound immobilized thereon;
- (a2) step of analyzing the fractions obtained in step (a1) with mass spectrometry;
- (a3) step of identifying each of the proteins in the fractions obtained in step (a1) based on the mass spectrometry information obtained in step (a2);
- (a4) step of quantitating each of the proteins in the fractions obtained in step (a1);
- (b1) step of analyzing a second group of proteins with mass spectrometry;
- (b2) step of identifying each protein in the second group of proteins based on the mass spectrometry information obtained in step (b1);
- (b3) step of quantitating each protein in the second group of proteins; and
- (c) step of obtaining, regarding each fraction obtained in step (a1), a ratio between the protein quantity obtained in step (a4) and the protein quantity obtained in step (b3), and comparing degrees of the binding ability of the plural kinds of proteins to the compound.

In the tenth embodiment, unlike in the fifth embodiment, each protein in the second group of proteins is quantitated without being fractionated into one or plural fractions using the carrier having the compound immobilized thereon. Except for this, the tenth embodiment is substantially the same as the fifth embodiment.

(11) Eleventh Embodiment

An eleventh embodiment of the present invention comprises the following steps for analyzing a binding ability of protein to a compound:
- (a1) step of fractionating a first group of proteins into plural fractions using a carrier having the compound immobilized thereon;
- (a2) step of analyzing the fractions obtained in step (a1) with mass spectrometry;
- (a3) step of identifying each of the proteins in the fractions obtained in step (a1) based on the mass spectrometry information obtained in step (a2);
- (a4) step of calculating an EMPAI of each of the proteins in the fractions obtained in step (a1);
- (b1) step of analyzing a second group of proteins with mass spectrometry;
- (b2) step of identifying each protein in the second group of proteins based on the mass spectrometry information obtained in step (b1);
- (b3) step of calculating an EMPAI of each protein in the second group of proteins; and
- (c) step of obtaining, regarding each fraction obtained in step (a1), a ratio between the EMPAI obtained in step (a4) and the EMPAI obtained in step (b3), and comparing degrees of the binding ability of the plural kinds of proteins to the compound.

In the eleventh embodiment, unlike in the sixth embodiment, the EMPAI of each protein in the second group of proteins is calculated without the second group of proteins being fractionated into one or plural fractions using the carrier having the compound immobilized thereon. Except for this, the eleventh embodiment is substantially the same as the sixth embodiment.

3. Analysis System

An analysis system of the present invention is for carrying out a method for analyzing a binding ability of protein to a compound, comprising the following means:

(1) Embodiment in which the samples are isotope-labeled before fractionation
- (a) means for fractionating a first group of isotope-labeled proteins into plural fractions using a carrier having the compound immobilized thereon;
- (b) means for fractionating a second group of proteins into one or plural fractions using a carrier having the compound immobilized thereon;
- (c) means for adding a certain amount of the one fraction obtained by means (b), or a certain amount of a mixture of all the fractions or a mixture of plural contiguous fractions among the fractions obtained by means (b), to each of the fractions obtained by means (a);
- (d) means for analyzing the fractions obtained by means (c) with mass spectrometry; and
- (e) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(2) Embodiment in which the samples for the internal standard fraction are isotope-labeled before fractionation
- (a) means for fractionating a first group of proteins into plural fractions using a carrier having the compound immobilized thereon;
- (b) means for fractionating a second group of isotope-labeled proteins into one or plural fractions using a carrier having the compound immobilized thereon;
- (c) means for adding a certain amount of the one fraction obtained by means (b), or a certain amount of a mixture of all the fractions or a mixture of plural contiguous fractions among the fractions obtained by means (b), to each of the fractions obtained by means (a);
(d) means for analyzing the fractions obtained by means (c) with mass spectrometry; and
(e) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(3) Embodiment in which the samples are labeled after fractionation
  (a) means for fractionating a first group of proteins into plural fractions using a carrier having the compound immobilized thereon;
  (b) means for fractionating a second group of proteins into one or plural fractions using a carrier having the compound immobilized thereon;
  (c) means for labeling the fractions obtained by means (a);
  (d) means for adding a certain amount of the one fraction obtained by means (b), or a certain amount of a mixture of all the fractions or a mixture of plural contiguous fractions among the fractions obtained by means (b), to each of the fractions labeled by means (c);
  (e) means for analyzing the fractions obtained by means (d) with mass spectrometry; and
  (f) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(4) Embodiment in which the samples for the internal standard fraction are fractionated and then labeled
  (a) means for fractionating a first group of proteins into plural fractions using a carrier having the compound immobilized thereon;
  (b) means for fractionating a second group of proteins into one or plural fractions using a carrier having the compound immobilized thereon;
  (c) means for labeling the one fraction obtained by means (b), or a mixture of all the fractions or a mixture of plural contiguous fractions among the fractions obtained by means (b);
  (d) means for adding a certain amount of the fraction or the mixture labeled by means (c) to each of the fractions obtained by means (a);
  (e) means for analyzing the fractions obtained by means (d) with mass spectrometry; and
  (f) means for, based on the mass spectrometry information, obtaining, regarding each fraction, an intensity ratio between a peak derived from a protein in the fraction obtained by means (a) and a peak derived from a protein in the fraction obtained by means (b), and comparing degrees of the binding ability of the plural kinds of proteins to the compound.

(5) Embodiment in which the test protein samples and the samples for the internal standard fraction are fractionated and then quantitated
  (a1) means for fractionating a first group of proteins into plural fractions using a carrier having the compound immobilized thereon;
  (a2) means for analyzing the fractions obtained by means (a1) with mass spectrometry;
  (a3) means for identifying each of the proteins in the fractions obtained by means (a1) based on the mass spectrometry information obtained by means (a2);
  (a4) means for quantitating each of the proteins in the fractions obtained by means (a1);
  (b1) means for fractionating a second group of proteins into one or plural fractions using a carrier having the compound immobilized thereon;
  (b2) means for analyzing the one fraction obtained by means (b1), or a mixture of all the fractions or a mixture of plural contiguous fractions among the fractions obtained by means (b1), with mass spectrometry;
  (b3) means for identifying each of the proteins in the one fraction or the mixture recited by means (b2) based on the mass spectrometry information obtained by means (b2);
  (b4) means for quantitating each of the proteins in the one fraction or the mixture recited by means (b2); and
  (c) means for obtaining, regarding each fraction obtained by means (a1), a ratio between the protein quantity obtained by means (a4) and the protein quantity obtained by means (b4), and comparing degrees of the binding ability of the plural kinds of proteins to the compound.

(6) Embodiment in which the test protein samples and the samples for the internal standard fraction are fractionated and then the EMPAI of each protein is calculated
  (a1) means for fractionating a first group of proteins into plural fractions using a carrier having the compound immobilized thereon;
  (a2) means for analyzing the fractions obtained by means (a1) with mass spectrometry;
  (a3) means for identifying each of the proteins in the fractions obtained by means (a1) based on the mass spectrometry information obtained by means (a2);
  (a4) means for calculating an EMPAI of each of the proteins in the fractions obtained by means (a1);
  (b1) means for fractionating a second group of proteins into one or plural fractions using a carrier having the compound immobilized thereon;
  (b2) means for analyzing the one fraction obtained by means (b1), or a mixture of all the fractions or a mixture of plural contiguous fractions among the fractions obtained by means (b1), with mass spectrometry;
  (b3) means for identifying each of the proteins in the one fraction or the mixture recited by means (b2) based on the mass spectrometry information obtained by means (b2);
  (b4) means for calculating an EMPAI of each of the proteins in the one fraction or the mixture recited by means (b2); and
  (c) means for obtaining, regarding each fraction obtained by means (a1), a ratio between the EMPAI obtained by means (a4) and the EMPAI obtained by means (b4), and comparing degrees of the binding ability of the plural kinds of proteins to the compound.

In the above embodiments of the system of the present invention, the samples for the internal standard fraction are fractionated using a carrier having a compound immobilized thereon. Embodiments in which the samples for the internal standard fraction are used without being fractionated using a carrier having a compound immobilized thereon as follows are also encompassed in the present invention.

(7) Embodiment in which the second group of proteins for the internal standard fraction in the embodiment (1) of the system are added in a certain amount to each of the fractions obtained by means (a) without being fractionated into one or plural fractions using a carrier having the compound immobilized thereon
  (a) means for fractionating a first group of isotope-labeled proteins into plural fractions using a carrier having the compound immobilized thereon;
  (b) means for adding a certain amount of a second group of proteins to each of the fractions obtained by means (a);
  (c) means for analyzing the fractions obtained by means (b) with mass spectrometry; and
  (d) means for, based on the mass spectrometry information, obtaining, regarding each fraction, an intensity ratio between a peak derived from a protein in the fraction obtained by means (a) and a peak derived from a protein in the second group of proteins, and comparing degrees of the binding ability of the plural kinds of proteins to the compound.

(8) Embodiment in which the second group of isotope-labeled proteins for the internal standard fraction in the embodiment (2) of the system are added in a certain amount to each of the fractions obtained by means (a) without being fractionated into one or plural fractions using a carrier having the compound immobilized thereon
  (a) means for fractionating a first group of proteins into plural fractions using a carrier having the compound immobilized thereon;
  (b) means for adding a certain amount of a second group of isotope-labeled proteins to each of the fractions obtained by means (a);
  (c) means for analyzing the fractions obtained by means (b) with mass spectrometry; and
  (d) means for, based on the mass spectrometry information, obtaining, regarding each fraction, an intensity ratio between a peak derived from a protein in the fraction obtained by means (a) and a peak derived from a protein in the second group of proteins, and comparing degrees of the binding ability of the plural kinds of proteins to the compound.

(9) Embodiment in which the second group of proteins for the internal standard fraction in the embodiment (3) of the system are added in a certain amount to each of the fractions obtained by means (b) without being fractionated into one or plural fractions using a carrier having the compound immobilized thereon
  (a) means for fractionating a first group of proteins into plural fractions using a carrier having the compound immobilized thereon;
  (b) means for labeling the fractions obtained by means (a);
  (c) means for adding a certain amount of a second group of proteins to each of the fractions labeled by means (b);
  (d) means for analyzing the fractions obtained by means (c) with mass spectrometry; and
  (e) means for, based on the mass spectrometry information, obtaining, regarding each fraction, an intensity ratio between a peak derived from a protein in the fraction obtained by means (a) and a peak derived from a protein in the second group of proteins, and comparing degrees of the binding ability of the plural kinds of proteins to the compound.

(10) Embodiment in which each protein in the second group of proteins in the embodiment (5) of the system is quantitated without being fractionated into one or plural fractions using a carrier having the compound immobilized thereon
  (a1) means for fractionating a first group of proteins into plural fractions using a carrier having the compound immobilized thereon;
  (a2) means for analyzing the fractions obtained by means (a1) with mass spectrometry;
  (a3) means for identifying each of the proteins in the fractions obtained by means (a1) based on the mass spectrometry information obtained by means (a2);
  (a4) means for quantitating each of the proteins in the fractions obtained by means (a1);
  (b1) means for analyzing a second group of proteins with mass spectrometry;
  (b2) means for identifying each protein in the second group of proteins based on the mass spectrometry information obtained by means (b1);
  (b3) means for quantitating each protein in the second group of proteins; and
  (c) means for obtaining, regarding each fraction obtained by means (a1), a ratio between the protein quantity obtained by means (a4) and the protein quantity obtained by means (b3), and comparing degrees of the binding ability of the plural kinds of proteins to the compound.

(11) Embodiment in which the EMPAI of each protein in the second group of proteins in the embodiment (6) of the system is calculated without the second group of proteins being fractionated into one or plural fractions using a carrier having the compound immobilized thereon
  (a1) means for fractionating a first group of proteins into plural fractions using a carrier having the compound immobilized thereon;
  (a2) means for analyzing the fractions obtained by means (a1) with mass spectrometry;
  (a3) means for identifying each of the proteins in the fractions obtained by means (a1) based on the mass spectrometry information obtained by means (a2);
  (a4) means for calculating an EMPAI of each of the proteins in the fractions obtained by means (a1);
  (b1) means for analyzing a second group of proteins with mass spectrometry;
  (b2) means for identifying each protein in the second group of proteins based on the mass spectrometry information obtained by means (b1);
  (b3) means for calculating an EMPAI of each protein in the second group of proteins; and
  (c) means for obtaining, regarding each fraction obtained by means (a1), a ratio between the EMPAI obtained by means (a4) and the EMPAI obtained by means (b3), and comparing degrees of the binding ability of the plural kinds of proteins to the compound.

(12) Details of the System of the Present Invention

Figure 3:
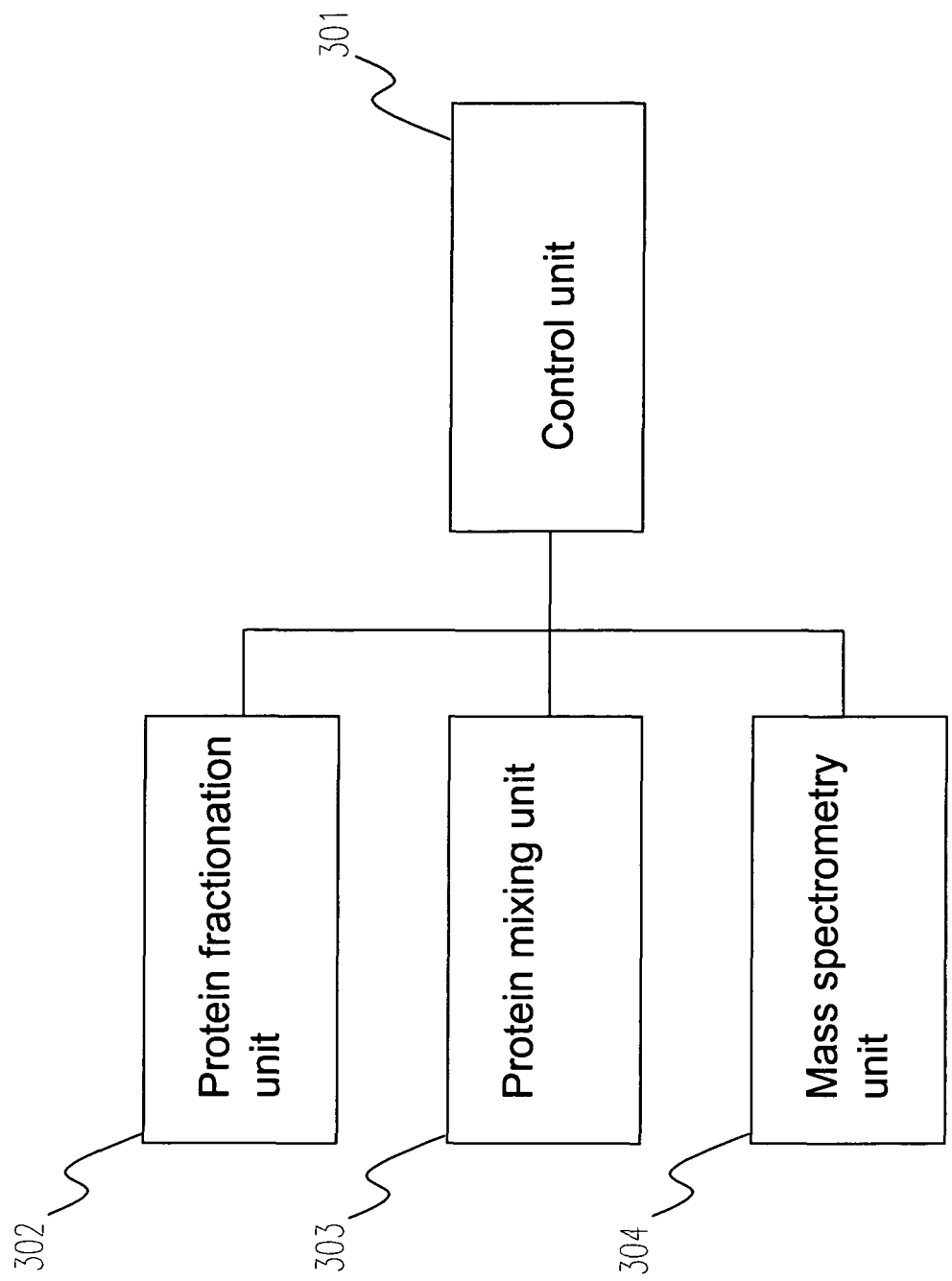
FIG. 3 is a block diagram showing an exemplary structure of a system of the present invention.

FIG. 3 is a block diagram showing an exemplary structure of a system according to the present invention. In the example shown in FIG. 3, the system according to the present invention includes a control unit 301, a protein fractionation unit 302, a protein mixing unit 303, and a mass spectrometry unit 304.

The control unit 301 controls the entire operation of each unit necessary for carrying out the method according to the present invention. The protein fractionation unit 302, the protein mixing unit 303 and the mass spectrometry unit 304 are each connected to the control unit 301, and are each controlled by the control unit 301 so as to operate independently or in association with one another. For example, for carrying out the method according to the present invention mainly in a batch system, the units (the protein fractionation unit 302, the protein mixing unit 303 and the mass spectrometry unit 304) are each controlled independently, and the control unit 301 instructs each unit to perform a respective operation. For carrying out the method according to the present invention mainly in a continuous flow system, the control unit 301 monitors the operation of each unit, for example, how each unit proceeds with the operation, and the units are controlled in association with one another.

The protein fractionation unit 302 is a unit for eluting proteins bound to the compound immobilized on carriers in the column, and includes a carrier for fractionating the first group of proteins into plural fractions, a carrier for fractionating the second group of proteins into one or plural fractions, a cell culture device, a cell crushing device, an eluting device for the compound bound to the carrier, a recovery device for the eluted proteins (fractionated proteins), and the like. The elements included in the fractionation unit are controlled independently or in association with one another by an instruction from the control unit 301.

The protein mixing unit 303 is a unit for mixing the proteins fractionated by the protein fractionation unit 302. For example, in the first embodiment described above, the protein mixing unit 303 controls the step of adding a certain amount of one fraction, or a certain amount of a mixture of all the fractions or a mixture of plural contiguous fractions, derived from the second group of protein samples to the fractions derived from the first group of isotope-labeled protein samples. The protein mixing unit 303 is connected to the control unit 301, and performs mixing upon receiving an instruction on the amount to be added and the like from the control unit 301.

The mass spectrometry unit 304 is a unit for analyzing the mixed proteins with mass spectrometry, and includes a spotter for spotting the mixed proteins on a measurement plate, a tray for putting the measurement plate on a mass spectrometry device and the like. The elements in the mass spectrometry unit 304 are connected to the control unit 301, and executes mass spectrometry in accordance with an instruction from the control unit 301.

Figure 4:
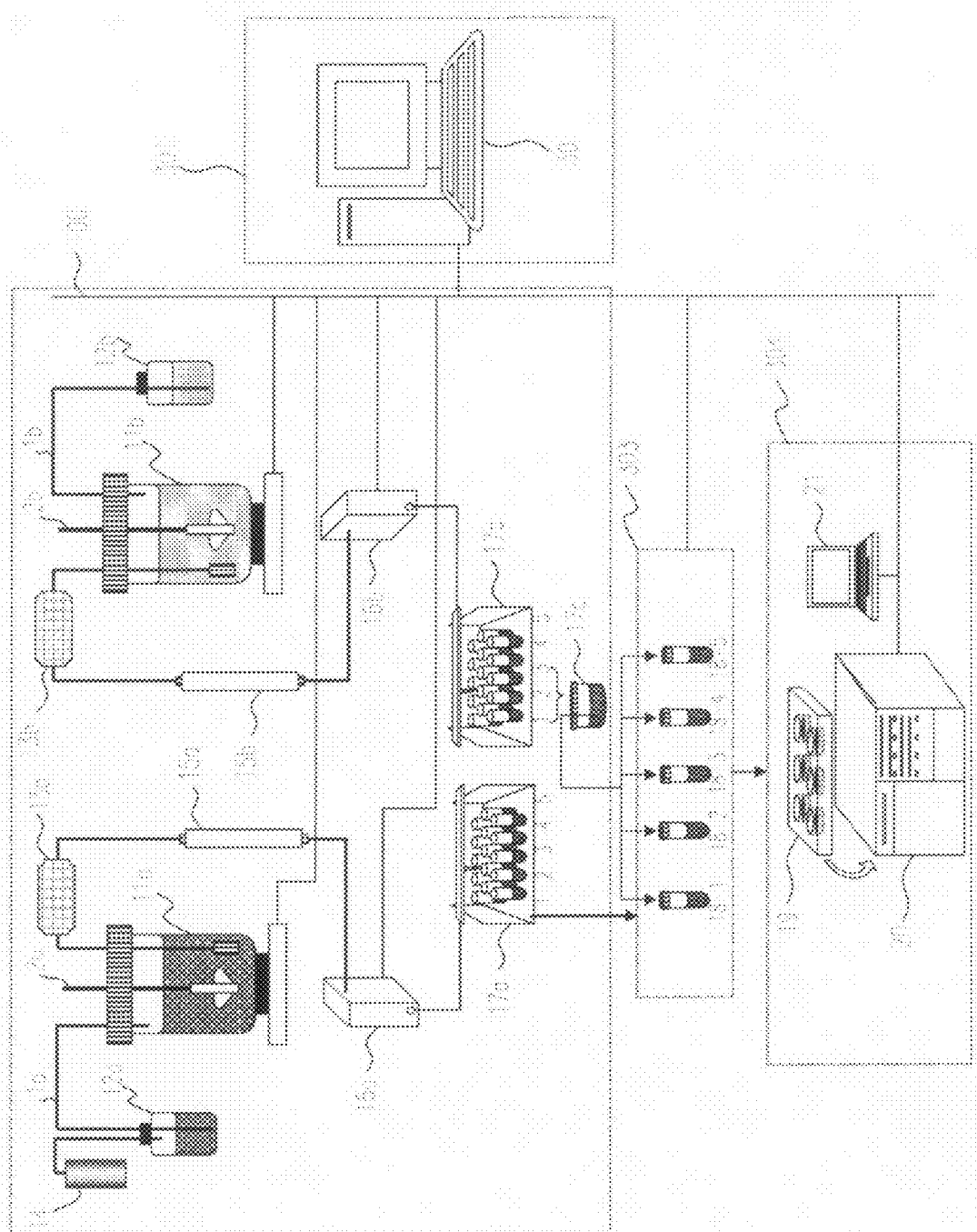
FIG. 4 is a schematic view showing an example of each unit of the system of the present invention.

FIG. 4 is a schematic view showing an embodiment of the units.

As shown in FIG. 4, the protein fractionation unit 302 includes, for example, culture devices 11a and 11b, culture liquid bottles 12a and 12b, cell crushing devices 13a and 13b, a labeling device 14, carriers 15a and 15b having a compound immobilized thereon, protein fractionation control devices (hereinafter, also referred to as "control devices") 16a and 16b, purified protein separators 17a and 17b, a mixing device 17c and the like.

The culture devices 11a and 11b are devices for culturing cells, and culture cells for a predetermined time period while adjusting the temperature, $CO_2$ concentration and the like.

The culture devices 11a and 11b are respectively connected to the culture liquid bottles 12a and 12b. The culture liquid bottles 12a and 12b may supply a culture liquid to the culture devices via tubes 11a and 11b, respectively. The culture devices 11a and 11b may respectively include stirring blades 2a and 2b. The culture devices 11a and 11b are shown here as vessels for culturing floating cells, but this is merely one embodiment for illustrating the system according to the present invention. The present invention is not limited to this. For culturing cells adhering to the culture plates, those skilled in the art could select culture devices in accordance with the purpose. The culture devices 11a and 11b are connected to the control unit 301 via a LAN 100.

The culture liquid bottles 12a and 12b are vessels for storing a culture liquid for culturing cells. In the first embodiment and the seventh embodiment of the present invention, the culture liquid bottle 12a contains amino acids for isotope-labeling the first group of proteins and the like in a mixed state. As shown in FIG. 4, the labeling device 14 may be connected to the culture liquid bottle 12a. The culture liquid bottles 12a and 12b may be connected to the control unit 301 via the LAN 100.

The cell crushing devices 13a and 13b are devices for crushing cultured cells to obtain proteins. The cell crushing devices 13a and 13b perform the step of collecting the cells from the culture devices 11a and 11b and crushing the cells, thereby obtaining a suspension of proteins. The cell crushing devices 13a and 13b may be connected to the control unit 301 via the LAN 100.

The labeling device 14 is a device for labeling (for example, isotope-labeling) protein samples or protein fractions obtained by fractionation. FIG. 4 shows an embodiment in which the labeling device 14 for labeling protein samples before fractionation is connected to the culture liquid bottle 12a. In the second embodiment of the present invention, the samples for the internal standard fraction are isotope-labeled before fractionation. In this case, the labeling device 14 may be connected to a culture liquid for culturing the samples for the internal standard fraction (the culture liquid bottle 12b).

In the eighth embodiment of the present invention, the samples for the internal standard fraction are isotope-labeled before being added to the fractions derived from the first group of proteins. In this case, the labeling device 14 may be connected to a culture liquid for culturing the samples for the internal standard fraction (the culture liquid bottle 12b).

In the third and fourth embodiments of the present invention, the test samples or the samples for the internal standard fraction are labeled after fractionation. For labeling the test samples, the labeling device 14 may be connected between the carrier 15a and the control device 16a, between the control device 16a and the purified protein separator 17a, or after the purified protein separator 17a. For labeling the samples for the internal standard fraction, the labeling device 14 may be connected between the carrier 15b and the control device 16b, between the control device 16b and the purified protein separator 17b, after the purified protein separator 17b, or after the mixing device 17c.

In the ninth embodiment of the present invention, the test samples are labeled after fractionation. In this case, the labeling device 14 may be connected between the carrier 15a and the control device 16a, between the control device 16a and the purified protein separator 17a, or after the purified protein separator 17a.

According to the present invention, the labeling device 14 is not limited to the above-described embodiments and may be in other embodiments for achieving the object of the present invention as easily understood by those skilled in the art. The labeling device 14 may be connected to the control unit 301 via the LAN 100.

In the fifth, sixth, tenth and eleventh embodiments of the present invention, the proteins do not need to be labeled. In this case, the protein fractionation unit 302 does not need to include the labeling device 14.

The carriers 15a and 15b are columns for purifying the proteins, and have a substance having a binding ability to protein immobilized thereon.

In accordance with an instruction from the control unit 301, the control devices 16a and 16b perform the step of introducing the proteins into the carriers 15a and 15b having a compound immobilized thereon, and also passing the eluting solvent to send the eluted protein fractions to the purified protein separators 17a and 17b. The eluting solvent may be flown to the carriers such that the concentration of the solvent has a gradient, or solvents having concentrations different in a step-by-step manner may be flown to the carriers. The control devices 16a and 16b may be connected to the control unit 301 via the LAN 100.

The purified protein separators 17a and 17b are devices for separating proteins obtained in one fractionation step and proteins obtained in the other fractionation step from each other and thus obtaining fractions. In some cases, the purified protein separators 17a and 17b may temporarily store the fractions. For an internal standard fraction, the mixing device 17c may be provided for mixing all the fractions or plural contiguous fractions of the protein fractions.

FIG. 4 shows one type of fractionation step. Alternatively, plural systems may be provided in parallel so as to allow plural kinds of fractionation steps to be performed. In this way, proteins derived from plural different kinds of cells can be fractionated.

In the embodiment shown in FIG. 4, the purified protein separators 17a and 17b are controlled by the control devices 16a and 16b, but the present invention is not limited to this. The purified protein separators 17a and 17b may be connected to the control unit 301 via the LAN 100 independently from the control devices 16a and 16b.

In the seventh, eighth, ninth, tenth and eleventh embodiments of the present invention, the samples for the internal standard fraction are used without being fractionated by a carrier having a compound immobilized thereon. In this case, the protein fractionation unit 302 does not need to include none of the carrier 15b, the control unit 16b, the purified protein separator 17b and the mixing device 17c.

In FIG. 4, the protein mixing unit 303 is a unit for adding the fractions derived from the second group of proteins to the fractions derived from the first group of proteins obtained as a result of the fractionation by the protein fractionation unit 302. In accordance with an instruction from the control unit 301, the protein mixing unit 303 selects fractions arranged in the purified protein separator 17a and adds a certain amount of the fractions arranged in the purified protein separator 17b or the mixing device 17c. FIG. 4 shows an exemplary embodiment in which a mixture of fractions 1 through fraction 3 arranged in the purified protein separator 17b to tubes (tubes 18-1 through 18-5) respectively containing the eluted fractions 1 through 5 (fractions from the purified protein separator 17a) via the mixing device 17c.

In the fifth, sixth, tenth and eleventh embodiments of the present invention, the fractions derived from the first group of proteins, and the fractions derived from the second group of proteins or the second group of proteins, are analyzed with mass spectrometry without the first and second groups of proteins being added together. In this case, the operation in the protein fractionation unit 302 may be followed by the operation in the mass spectrometry unit 304 with the operation in the protein mixing unit 303 being skipped. Therefore, in these embodiments, the system of the present invention does not need to include the protein mixing unit 303.

The mass spectrometry unit 304 is a unit for analyzing one or plural kinds of proteins as a target of mass spectrometry. In accordance with an instruction from the control unit 301, the mass spectrometry unit 304 spots a sample mixed by the protein mixing unit 303 on a plate 19 for mass spectrometry and executes mass spectrometry using a mass spectrometry device 20. For transferring the plate 19 to the mass spectrometry device 20, a computer-controlled robot-type sample handling device is also usable.

Mass spectrometry is executed in accordance with an instruction from the control unit 301 via the LAN 100. Alternatively, the mass spectrometry may be executed by a computer 21 provided as an accessory to the mass spectrometry device 20.

Mass spectrometry information is transmitted to the control unit 301 via the LAN 100, and is processed to obtain an identification profile, an intensity ratio profile, a binding ability ratio profile, a mass ratio profile, and an EMPAI ratio profile of proteins.

The control unit 301 is a central control unit for operating the system according to the present invention, and includes a central computer 30, an internet communication line and the like.

The control unit 301 identifies the proteins, determines the intensity ratio and the binding ability ratio between the isotope-labeled peak and the non-isotope-labeled peak, and displays the results in a display device in the control unit 301. Alternatively, based on the information on the identified proteins, the control unit 301 determines the protein quantity ratio or the EMPAI ratio between each of the proteins in the test fractions and each of the proteins in the internal standard fraction using the index EMPAI, and displays the results in the display device in the control unit 301. Each piece of data is automatically organized by the control unit 301.

Figure 5:
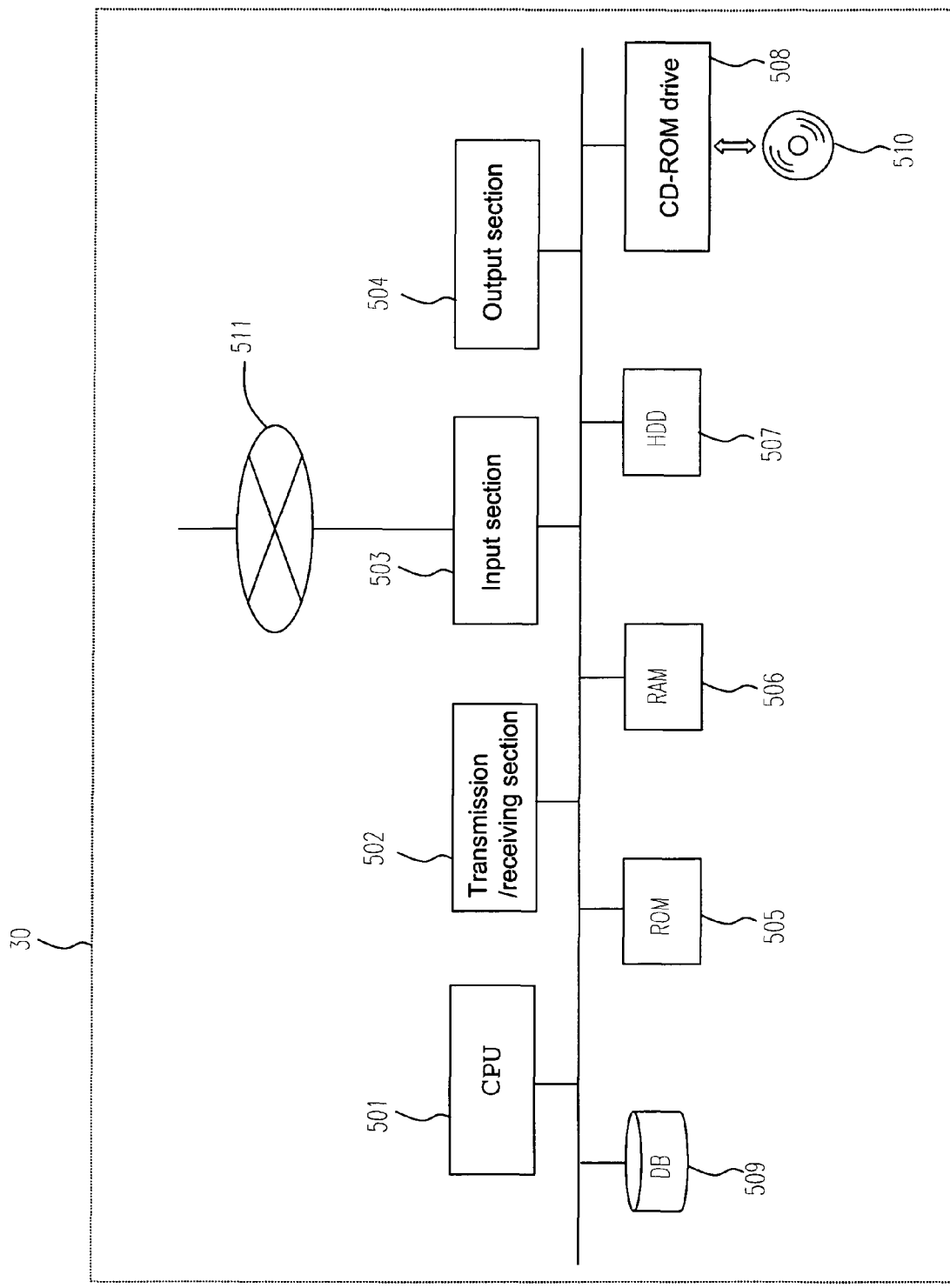
FIG. 5 shows an exemplary structure of a control unit in detail.

FIG. 5 is an exemplary detailed structural view of the control unit 301. As shown in FIG. 5, the central computer 30 includes a CPU 501, a transmission/receiving section 502, an input section 503, an output section 504, a ROM 505, a RAM 506, a hard disc drive (HDD) 507, a CD-ROM drive 508, and a protein database (hereinafter, referred to as "DB") 509.

The CPU 501 controls the entire operation of the system according to the present invention, and also records data on the mass spectrometry results, data on the identified protein, intensity ratio data, binding ability data and the like on the DB 509. The CPU 501 may control the communication of the transmission/receiving section 502 and check the data stored on the DB 509 against data of other proteins via the Internet 511.

In accordance with an instruction from the CPU 501, the transmission/receiving section 502 performs data transmission and receiving between the protein fractionation unit 302, the protein mixing unit 303, and the mass spectrometry unit 304.

The input section 503 includes a keyboard, a mouse, a touch panel or the like, and is operated when the user inputs information or updates the database. The output section 504 includes an LCD (liquid crystal display) or the like. For updating various databases, the output section 504 converts the code data from the CPU 501 into display data each time the code data is received, and displays the data. The ROM 505 stores a processing program of the system according to the present invention. The RAM 506 temporarily stores data necessary for processing executed by the system according to the present invention. The HDD 507 is a drive for storing mass spectrometry data and the like. In accordance with an instruction from the CPU 501, the CD-ROM drive 508 reads a program or the like necessary for executing the processing by the system according to the present invention (for executing the processing in various embodiments), which is stored on a CD-ROM 510, and writes the program onto the RAM 506 or the like. Instead of the CD-ROM, a rewritable medium such as a CD-R, CD-RW or the like may be used as a storage medium. In that case, a drive for CD-R or CD-RW is provided instead of the CD-ROM drive 508. Instead of the above-mentioned mediums, a DVD, MO, flash memory stick or the like may be used and a corresponding drive may be provided.

The central computer 30 communicates with the protein fractionation unit 302, the protein mixing unit 303, and the mass spectrometry unit 304, and transmits control information such that these units function. The central computer 30 also receives the protein identification results and the protein mass spectrometry results, and displays the identification results including the intensity ratio, the binding ability ratio, the protein quantity ratio, the EMPAI ratio and the like.

Figure 6:
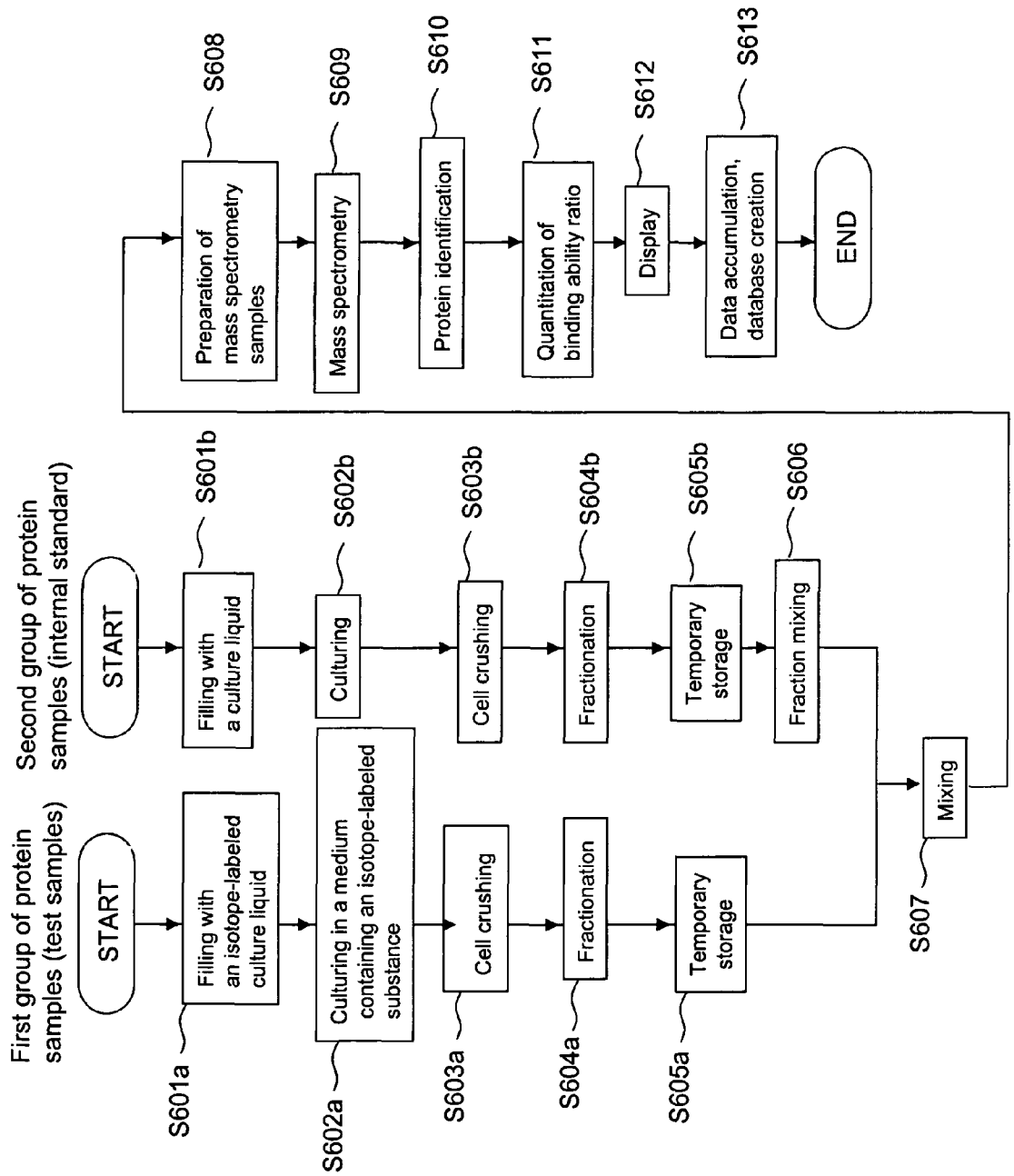
FIG. 6 is a flowchart showing an exemplary operation of the control unit.

Hereinafter, an operation of the control unit (first embodiment) will be described with reference to the drawing (FIG. 6).

The central computer 30 of the control unit 301 instructs a filling device to fill one culture device 11a with a culture liquid, a protein sample (cell) and other reagents necessary to carry out the present invention, and also instructs the labeling device 14 to add an isotope-labeled substance (isotope-labeled amino acid, etc.) necessary for labeling proteins. The labeling device 14 performs the addition of the isotope-labeled substance (S601a). In parallel, the central computer 30 instructs the sample filling device (not shown) to fill the other culture device 11b with a culture liquid, a sample (cell) and other reagents necessary to carry out the present invention. The filling device (not shown) performs the filling operation (S601b). When each of the culture devices 11a and 11b is filled with the culture liquid and the like, the central computer 30 instructs each culture device 11a, 11b to culture under predetermined conditions. Each culture device 11a, 11b performs the culture operation (S602a, S602b).

The "predetermined conditions" include the culturing time, the culturing temperature, the $CO_2$ concentration, whether or not to stir, and the like. When the culture operation under the predetermined conditions is completed, the central computer 30 instructs the cell crushing devices 13a and 13b to perform the cell crushing step. The cell crushing devices 13a and 13b perform the cell crushing operation (S603a, S603b). After the cell sampled from the medium containing the isotope-labeled substance is crushed in S603a, the central computer 30 instructs the carrier 15a having a predetermined substance (compound) immobilized thereon to perform the protein fractionation step. The carrier fractionates the proteins (first group of test proteins) (S604a). After the cell sampled from the medium not containing the isotope-labeled substance is crushed in S603b, the central computer 30 instructs the carrier 15b having a predetermined compound immobilized thereon to perform the protein fractionation step. The carrier fractionates the proteins (the second group of proteins for the internal standard fraction) (S604b). After the protein fractionation is completed, the central computer 30 instructs the protein fractionation control devices 16a and 16b to separate the protein samples into the purified protein separators 17a and 17b and temporarily store the protein samples in preparation of the subsequent mixing (S606, S607). The control devices perform the separation and temporary storage (S605a, S605b). Whether or not to perform the temporary storage is optional. Next, the central computer 30 instructs the mixing device 17c to mix all the fractions derived from the second group of proteins for the internal standard fraction or to mix plural contiguous fractions derived therefrom, and the mixing device 17c mixes the protein fractions (S606). When only one fraction is obtained as a result of the fractionation, the mixing device 17c does not mix the fractions derived from the second group of protein. Then, the central computer 30 instructs the protein mixing unit 303 to add the protein fractions for the internal standard fraction to each of the test protein fractions, and the protein mixing unit 303 adds a certain amount of the protein fractions for the internal standard fraction to each of the test protein fractions and mixes the fractions (S607).

When the mixing in S607 is completed, the central computer 30 instructs to prepare a sample for mass spectrometry (S608). Whether or not to perform the preparation is optional. Next, the central computer 30 instructs the spotter (not shown) to spot the prepared sample to a mass spectrometry plate (e.g., the plate 19 in FIG. 4) and instructs the mass spectrometry device to start the mass spectrometry of the sample. The spotter performs the spotting operation, and the mass spectrometer starts the mass spectrometry (S609).

The central computer 30 identifies the proteins (S610), and finds the intensity ratio between the peak with labeling and the peak without labeling of each protein and quantitates the binding ability ratio of the compound to the proteins (S611). The data on the protein identification results and the intensity ratio are transmitted to the central computer 30, and the output device or the computer display presents the identification results and the intensity ratio (S612), and also creates rankings of the binding ability of proteins bindable to a compound.

The central computer 30 checks the data on the intensity ratio and the identification results against the existing information, and accumulates the data on the hard disc for creating a database (S613).

Hereinafter, the present invention will be described more specifically by way of examples, but the present invention is not limited to these examples.

EXAMPLES (1) Production of an Affinity Chromatography Having a Compound Immobilized Thereon About 10 mg of the compound represented by formula (1):

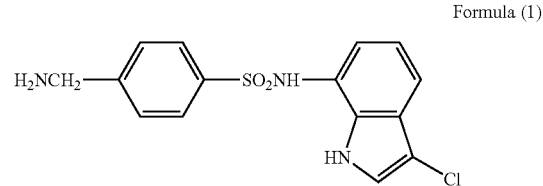

Formula (1)

was dissolved in 4 mL of tetrahydrofuran (THF) and 4 mL of methanol (MeOH), and 4 mL of water was added thereto.

6 mL of the resultant solution was diluted with 18 mL of THF/MeOH/Water=1/1/1 (v/v/v), and was added to 25 mL of Affi-gel 10 (produced by BioRad, Cat No. 153-6099), which had been washed with THF/MeOH/Water=1/1/1 (v/v/v) beforehand.

To the resultant substance, 100 μL of triethylamine (produced by Tokyo Chemical Industry Co., Ltd., Cat No. T0424) was added thereto and incubated at room temperature for 2 hours. Then, 500 μL of 2-aminoethanol (produced by Tokyo Chemical Industry Co., Ltd., Cat No. A0297) was added thereto and incubated at room temperature for 2 hours. The resultant gel was fully washed with THF/MeOH/Water=1/1/1 (v/v/v), and was stored at 4° C. after replacement with a methanol solution. The resultant gel was set to be used as an affinity gel. By this reaction, the compound represented by formula (1) was bound at a ratio of about 0.2 mg for 1 mL of gel. A column was filled with about 0.9 ml of the produced affinity gel. Thus, an affinity chromatography column was produced.

(2) Preparation of Cells

Human colon glandular cancer cell line HCT116 (ATCC) was cultured. Used as a medium was RPMI-1640 (Sigma, R-7130) containing 10% fetal calf serum (MOREGATE, BATCH 32300102), 100 U/ml of penicillin G; and 100 μg/ml of streptomycin (Invitrogen, 15140-122). As for the RPMI-1640 medium, a powder medium which contains none of L-glutamine, L-lysine, L-methionine, L-leucine, and sodium hydrogen carbonate was selected. Then, components absent in the medium were added. The absent components were added as follows. L-glutamine (produced by Sigma, G-8540), L-lysine (produced by Sigma, L-9037), L-methionine (produced by Sigma, M-5308), and sodium hydrogen carbonate (Wako Pure Chemical Industries, Ltd., 191-01305) were added in 0.3 g/L, 0.04 g/L, 0.015 g/L, and 2 g/L, respectively; and then naturally-occurring L-leucine and L-leucine labeled with a stable isotope $^{13}C$ (six) (Cambridge Isotope Laboratories, CLM-2262) were separately added in 0.05 g/L. Each medium thus prepared was used to culture cells in 5% $CO_2$ at 37° C. The cells obtained by such culturing were used in the following tests as cells cultured in a naturally-occurring medium and cells cultured in a stable isotope medium, respectively.

(3) Extraction of Proteins

Cells cultured in the naturally-occurring medium were provided in an amount corresponding to ten 15-cm diameter plates. Cells cultured in the stable isotope medium were provided in an amount corresponding to ten 15-cm diameter plates. The cells were collected. The cells were solubulized with about 2 ml of M-PER (PIERCE, 78501) per 15-cm diameter plate. Insoluble fractions were removed by centrifugation to prepare soluble fractions. The soluble fractions thus obtained were set to be used as a protein extract liquid metabolically labeled with a stable isotope and a protein extract liquid not metabolically labeled with a stable isotope, respectively. To these protein extract liquids (about 20 ml each), a quadruple amount of PBS was added (final amount: about 100 ml each).

(4) Affinity Column Operation

Next, about 0.9 ml of affinity gel was put into an open column, and a diluted protein extract liquid metabolically labeled with a stable isotope was added to the open column from above and was naturally dropped. Then, 10 ml of PBS containing 1 M NaCl was flown to this column. Next, 7 ml of PBS containing 1 M urea and 0.01% CHAPS, 7 ml of PBS containing 2 M urea and 0.01% CHAPS, 7 ml of PBS containing 4 M urea and 0.01% CHAPS, and 7 ml of PBS containing 8 M urea and 0.01% CHAPS were sequentially flown, and the eluted fractions were collected (4 fractions in total).

In parallel with the above operation, a diluted protein extract liquid not metabolically labeled with a stable isotope was added to 0.9 ml of affinity gel from above and was naturally dropped. Then, 10 ml of PBS containing 1 M NaCl was flown to this column. Next, 12 ml of PBS containing 8 M urea and 0.01% CHAPS was flown, and the eluted fractions were collected to be used as an internal standard fraction.

(5) Treatment of Fractionated Samples 3 ml of the internal standard fraction was added to each of the four fractionated samples and mixed together. Each of the mixture liquids was concentrated to about 0.5 ml with Amicon Ultra-15 10,000MWCO (Millipore, Cat No. UFC901096), and then concentrated to about 25 μl with 0.5 ml of BIOMAX-10 K NMWL MEMBRANE (Millipore, Cat No. UFV5BGC00). The obtained substance was mixed with an equal amount of SDS-PAGE sample buffer. Then, the total amount thereof was separated with SDS-PAGE (DRC K.K., 5 to 20% T gel, 1 mm, 7 wells, 4 cm, 200 V), and digested with trypsin in a gel in an electrophoresis lane equally divided into 12. The resultant solution was set to be used as a digested protein solution (H. Katayama, T. Tabata, Y Ishihama, T. Sato, Y Oda and T. Nagasu, Rapid Commun. Mass Spectrom., 18, 2388-2394 (2004)).

(6) Measurement with LC/MS

The digested protein solution was dissolved in 5% acetonitrile containing 8 μl of 0.1% trifluoroacetic acid, and the resultant substance was set to be used as a protein solution, which is a target of LC/MS measurement. MS of LC/MS was performed using LCQ-Duo (produced by Thermo Electron). LC of LC/MS was performed as follows. A Lab-made ODS column (Y. Ishihama, J. Rappsilber, J. S. Andersen, M. Mann, J. Chromatogr A. 979, 233-239 (2002)) (inner diameter: 0.2 mm; length: about 15 cm) was used. 0.5% acetic acid was incorporated as a mobile phase. Over the first 1 minute, the acetonitrile concentration was reduced to 4%. Then, over the subsequent 35 minutes, the acetonitrile concentration was linearly increased to 20%. Then, within 0.1 minute, the acetonitrile concentration was increased to 80%, which was kept for 5 minutes. Then, the acetonitrile concentration was reduced to 0%. 12 minutes later, the next sample was implanted.

As the pump, an LC-10A series device of Shimadzu Corporation was used with the ROM being made compatible to the order of micrometers. As the mixing chamber, T connector of Barco was used instead of the Shimadzu chamber attached to the pump.

For the flow rate, the flow-splitting system was used. The flow rate in the column was adjusted to be about 0.5 to 1 μL per minute. The protein solution as the target of measurement was implanted in 3 μL to the column by Autosampler PAL of CTC. Ions obtained by directly spraying the eluted substance from the column outlet were transferred to the LTQ to perform the measurement. As a spray voltage, 2.4 kV was applied. The measurement was performed in the data dependent mode, with the Repeat of Dynamic Exclusion being set to 1. In order to maximize the number of times of scanning, the so-called double play mode was used for the measurement, without the zoom scan mode.

(7) Data Analysis

The proteins were automatically identified using X!Tandem (http://thegpm.org/GPM/index.html) and the NCBInr database. The program was partially modified such that the proteins could be searched using the NCBInr even with leucine labeled with a stable isotope (the molecular weight is increased by 6 per leucine).

Quantitation was to be performed at the peak of the peptides containing leucine. Therefore, only the peptides containing leucine were selected from the peptides identified by X!Tandem. In order to specify the elution position at the peptide peak (retaining time with HPLC=scanning number with MS), software for automatically selecting scanning information was constructed using the function of Mass Navigator co-developed with Mitsui Knowledge Industry Co., Ltd. Based on the scanning number information, the MS spectrum of the scanning number was extracted. Regarding the peak of the naturally-occurring leucine peptides and the peak of the isotope peptides, the following was obtained from the search result by X!Tandem: information on the parent ions (m(mass)/z(charge) value) when the MS/MS was performed; how many leucines were contained in the peptides; and how many charges were present. Peaks forming a pair were found, and the peak intensity ratio thereof was automatically calculated. In this manner, proteins were identified and the peak intensity ratio was calculated using the constructed software.

(8) Results

The results are shown in Table 1.

TABLE 1

| locus link.locus ID | gene symbol | product | 1M Urea | 2M Urea | 4M Urea | 8M Urea |
|---|---|---|---|---|---|---|
| 191 | AHCY | S-adenosylhomocysteine hydrolase | 0.63 | 0.99 | 1.88 | 3.27 |
| 4507 | MTAP | 5'-methylthioadenosine phosphorylase | 0.77 | 0.78 | 0.71 | 0.88 |
| 81848 | SPRY4 | sprouty homolog 4 | 3.70 | 1.17 | 0.83 | 0.67 |
| 10956 | OS9 | amplified in osteosarcoma isoform 2 precursor amplified in osteosarcoma isoform 3 precursor amplified in osteosarcoma isoform 4 precursor amplified in osteosarcoma isoform 1 precursor | 1.24 | 3.57 | 1.62 | 0.73 |
| 5110 | PCMT1 | protein-L-isoaspartate (D-aspartate) O-methyltransferase | 1.14 | 1.57 | 2.52 | 1.02 |

In Table 1, the numerical figures provided in the "Urea" sections of various concentrations each represent the peak intensity ratio (peak area of the labeled protein/peak area of the non-labeled protein). In Table 1, as the concentration of urea is higher, the eluting power is stronger, and the numerical figure of the intensity ratio is larger, a larger amount is eluted in the corresponding fraction. In this example, elution was performed with four different concentrations of urea, i.e., 1 M, 2 M, 4 M and 8 M. Therefore, a protein having a higher peak in the fraction of 8 M urea has a higher binding ability to the compound represented by formula (1). Paying attention to the results of only the fraction of 8 M urea, a protein having a larger numerical figure is more concentrated in this fraction, namely, is bound more strongly.

In this example, AHCY has the highest peak in the 8 M urea fraction, PCMT1 has the highest peak in the 4 M urea fraction, OS9 has the highest peak in the 2 M urea fraction, and SPRY4 has the highest peak in the 1 M urea fraction (Table 1). Therefore, it is analyzed that the binding ability of the proteins to the compound represented by formula (1) is ordered, from highest to lowest, as AHCY, PCMT1, OS9 and SPRY4. Comparing the peak intensity ratios of the proteins in the 8 M urea fraction, the numerical figure is largest with AHCY and is decreased in the order of PCMT1, OS9 and SPRY4. Based on this also, it is analyzed that the binding ability of the proteins to the compound represented with formula (1) is ordered, from highest to lowest, as AHCY, PCMT1, OS9 and SPRY4. MTAP shows the value of about 0.8 in all the four fractions. Since the highest peak is not clear, the eluting fraction cannot be clearly specified.

INDUSTRIAL APPLICABILITY

The present invention makes it possible to create rankings of the binding ability of plural kinds of substances (proteins) bindable to a compound. The method of the present invention makes it possible to analyze a binding ability of plural kinds of unknown substances to a compound. The method of the present invention is useful in being applicable even to the case where the target substance is unknown and the substances are not fully separated in a mixed sample.

The invention claimed is:

1. A method for analyzing binding ability of plural kinds of proteins to a compound, comprising the steps of:
   (a) fractionating a first group containing plural kinds of isotope-labeled proteins into plural fractions using a chromatography column comprising a carrier having the compound immobilized thereon;
   (b) fractionating a second group containing plural kinds of proteins into one or plural fractions using a chromatography column comprising a carrier having the compound immobilized thereon;
   (c) adding a certain amount of the one fraction obtained in step (b), a certain amount of a mixture of all the fractions obtained in step (b) or a certain amount of a mixture of plural contiguous fractions among the fractions obtained in step (b), to each of the fractions obtained in step (a) so as to obtain combined fractions, wherein each of the combined fractions is maintained separately from other combined fractions;
   (d) analyzing separately each of the combined fractions obtained in step (c) with mass spectrometry to obtain mass spectrometry protein peaks; and
   (e) obtaining, regarding each combined fraction obtained in step (c), an intensity ratio between protein peaks of the first group and protein peaks of the second group based on the mass spectrometry analysis of step (d) to determine in which fraction each protein is concentrated, and determining that a protein concentrated in a fraction which is eluted later from the column has a higher binding ability to the compound than a protein concentrated in a fraction which is eluted earlier from the column among the plural kinds of proteins, thereby creating rankings of the binding ability of the proteins to the compound.

2. A method for analyzing binding ability of plural kinds of proteins to a compound, comprising the steps of:
   (a) fractionating a first group containing plural kinds of proteins into plural fractions using a chromatography column comprising a carrier having the compound immobilized thereon;
   (b) fractionating a second group containing plural kinds of isotope-labeled proteins into one or plural fractions using a chromatography column comprising a carrier having the compound immobilized thereon;
   (c) adding a certain amount of the one fraction obtained in step (b), a certain amount of a mixture of all the fractions obtained in step (b) or a certain amount of a mixture of plural contiguous fractions among the fractions obtained in step (b), to each of the fractions obtained in step (a) so as to obtain combined fractions, wherein each of the combined fractions is maintained separately from other combined fractions;

(d) analyzing separately each of the combined fractions obtained in step (c) with mass spectrometry to obtain mass spectrometry protein peaks; and (e) obtaining, regarding each combined fraction produced in step (c), an intensity ratio between protein peaks of the first group and protein peaks of the second group based on the mass spectrometry analysis of step (d) to determine in which fraction each protein is concentrated, and determining that a protein concentrated in a fraction which is eluted later from the column has a higher binding ability to the compound than a protein concentrated in a fraction which is eluted earlier from the column among the plural kinds of proteins, thereby creating rankings of the binding ability of the proteins to the compound.

3. A method for analyzing binding ability of plural kinds of proteins to a compound, comprising the steps of:

(a) fractionating a first group containing plural kinds of proteins into plural fractions using a chromatography column comprising a carrier having the compound immobilized thereon;

(b) fractionating a second group containing plural kinds of proteins into one or plural fractions using a chromatography column comprising a carrier having the compound immobilized thereon;

(c) labeling the fractions obtained in step (a) with an isotope label;

(d) adding a certain amount of the one fraction obtained in step (b), a certain amount of a mixture of all the fractions obtained in step (b) or a certain amount of a mixture of plural contiguous fractions among the fractions obtained in step (b), to each of the fractions labeled in step (c) so as to obtain combined fractions, wherein each of the combined fractions is maintained separately from other combined fractions;

(e) analyzing separately each of the combined fractions obtained in step (d) with mass spectrometry to obtain mass spectrometry protein peaks; and (f) obtaining, regarding each combined fraction obtained in step (d), an intensity ratio between protein peaks of the first group and protein peaks of the second group based on the mass spectrometry analysis of step (e) to determine in which fraction each protein is concentrated, and determining that a protein concentrated in a fraction which is eluted later from the column has a higher binding ability to the compound than a protein concentrated in a fraction which is eluted earlier from the column among the plural kinds of proteins, thereby creating rankings of the binding ability of the proteins to the compound.

4. A method for analyzing binding ability of plural kinds of proteins to a compound, comprising the steps of:

(a) fractionating a first group containing plural kinds of proteins into plural fractions using a chromatography column comprising a carrier having the compound immobilized thereon;

(b) fractionating a second group containing plural kinds of proteins into one or plural fractions using a chromatography column comprising a carrier having the compound immobilized thereon;

(c) labeling, with an isotope label, the one fraction obtained in step (b), a mixture of all the fractions obtained in step (b) or a mixture of plural contiguous fractions among the fractions obtained in step (b);

(d) adding a certain amount of the fraction or the mixture labeled in step (c) to each of the fractions obtained in step (a) so as to obtain combined fractions, wherein each of the combined fractions is maintained separately from other combined fractions;

(e) analyzing separately each of the combined fractions obtained in step (d) with mass spectrometry to obtain mass spectrometry protein peaks; and (f) obtaining, regarding each combined fraction obtained in step (d), an intensity ratio between protein peaks of the first group and protein peaks of the second group based on the mass spectrometry analysis of step (e) to determine in which fraction each protein is concentrated, and determining that a protein concentrated in a fraction which is eluted later from the column has a higher binding ability to the compound than a protein concentrated in a fraction which is eluted earlier from the column among the plural kinds of proteins, thereby creating rankings of the binding ability of the proteins to the compound.

5. The method of claim 1, wherein step (a) of fractionating and/or step (b) of fractionating is performed by changing the strength of an eluting solvent.

6. The method of claim 1, further comprising the step of identifying each protein contained in each combined fraction based on the mass spectrometry analysis of step (d).

* * * * *